(12) United States Patent
Ahrens et al.

(10) Patent No.: US 11,408,885 B2
(45) Date of Patent: Aug. 9, 2022

(54) COMPOSITIONS AND MULTIPLEX ASSAYS FOR CHARACTERIZING ACTIVE PROTEASES AND THEIR INHIBITORS

(71) Applicant: Massachusetts Institute of Technology, Cambridge, MA (US)

(72) Inventors: Caroline Chopko Ahrens, Kennett Square, PA (US); Linda G. Griffith, Cambridge, MA (US); Steven Robert Tannenbaum, Brookline, MA (US); Christi Dionne Cook, Cambridge, MA (US); Ravindra Kodihalli, Acton, MA (US); Douglas A. Lauffenburger, Cambridge, MA (US); Evan L. Chiswick, Jamaica Plain, MA (US); Miles Miller, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 528 days.

(21) Appl. No.: 16/115,289

(22) Filed: Aug. 28, 2018

(65) Prior Publication Data
US 2019/0064167 A1   Feb. 28, 2019

Related U.S. Application Data

(60) Provisional application No. 62/585,918, filed on Nov. 14, 2017, provisional application No. 62/552,773, filed on Aug. 31, 2017.

(51) Int. Cl.
*G01N 33/573* (2006.01)
*G01N 33/535* (2006.01)
(Continued)

(52) U.S. Cl.
CPC ............. *G01N 33/573* (2013.01); *C12Q 1/37* (2013.01); *G01N 33/533* (2013.01);
(Continued)

(58) Field of Classification Search
CPC ............... G01N 33/573; G01N 33/535; G01N 33/54326; G01N 33/574; G01N 33/54313
See application file for complete search history.

(56) References Cited

U.S. PATENT DOCUMENTS

| | | |
|---|---|---|
| 4,310,408 A | 1/1982 | Rose |
| 4,499,052 A | 2/1985 | Fulwyler |

(Continued)

FOREIGN PATENT DOCUMENTS

| | | |
|---|---|---|
| WO | 2004/048935 | 6/2004 |
| WO | 2004048935 | 6/2004 |

(Continued)

OTHER PUBLICATIONS

Jana et al. Regulation of Matrix Metalloproteinase-2 Activity by COX-2-PGE2-pAKT Axis Promote Angiogenesis in Endometriosis. Plos One 11 (10): e0163540 1-18 (Oct. 3, 2016).*

(Continued)

*Primary Examiner* — Gailene Gabel
(74) *Attorney, Agent, or Firm* — Pabst Patent Group LLP

(57) ABSTRACT

Proteases regulate a wide range of normal cellular functions where dysregulated activity is observed in various diseases. Compositions and methods use protease activity multiplexed bead-based immunoassays to profile protease activity. This platform technology integrates protease activity measurements with total protein quantification techniques. It represents a significant improvement over existing detection techniques by allowing for multiplexed, sensitive active protease measurements in complex biological samples. Exemplary multiplexed detections are realized in a single assay using a minute sample amount (e.g., 5 µl) for active recombinant MMP-1, -2, -3, -7, 9, and 12 and those same MMPs in cell culture supernatant, menstrual fluid effluent, and peritoneal aspirates. This multiplexed platform achieves high level of sensitivities equal to or better than existing (Continued)

◂ Active MMP
○▭ Activity-based probe (e.g., biotin-tagged hydroxamate benzophenone)
◂ Capture antibody
) Encoded particle (e.g., color-coded bead)
☆ Dye for labeling the probe (e.g., fluorescent streptavidin)

leading single-plex detection strategies. It also allows for high throughput screening to identify inhibitors of proteases in complex, donor-derived samples.

13 Claims, 10 Drawing Sheets

(51) Int. Cl.
  *G01N 33/58* (2006.01)
  *G01N 33/543* (2006.01)
  *G01N 33/533* (2006.01)
  *C12Q 1/37* (2006.01)
  *G01N 33/574* (2006.01)
  *G16B 99/00* (2019.01)
  *G16C 99/00* (2019.01)

(52) U.S. Cl.
  CPC ..... *G01N 33/535* (2013.01); *G01N 33/54306* (2013.01); *G01N 33/54313* (2013.01); *G01N 33/54326* (2013.01); *G01N 33/58* (2013.01); *C12Y 304/24007* (2013.01); *C12Y 304/24024* (2013.01); *C12Y 304/24035* (2013.01); *G01N 33/574* (2013.01); *G16B 99/00* (2019.02); *G16C 99/00* (2019.02)

(56) References Cited

U.S. PATENT DOCUMENTS

| | | | |
|---|---|---|---|
| 4,753,875 A | 6/1988 | Ryan | |
| 5,028,545 A | 7/1991 | Soini | |
| 5,476,766 A | 12/1995 | Gold | |
| 5,503,978 A | 4/1996 | Schneider | |
| 5,631,146 A | 5/1997 | Szostak | |
| 5,731,424 A | 3/1998 | Toothman | |
| 5,780,228 A | 7/1998 | Parma | |
| 5,792,613 A | 8/1998 | Schmidt | |
| 5,795,721 A | 8/1998 | Rabin | |
| 5,846,713 A | 12/1998 | Pagratis | |
| 5,858,660 A | 1/1999 | Eaton | |
| 5,861,254 A | 1/1999 | Schneider | |
| 5,864,026 A | 1/1999 | Jensen | |
| 5,869,641 A | 2/1999 | Jayasena | |
| 5,926,387 A | 7/1999 | Furst | |
| 5,958,691 A | 9/1999 | Pieken | |
| 5,981,180 A * | 11/1999 | Chandler | G01N 15/1012 |
| | | | 435/6.12 |
| 6,001,988 A | 12/1999 | Parma | |
| 6,011,020 A | 1/2000 | Gold | |
| 6,013,443 A | 1/2000 | Heilig | |
| 6,020,130 A | 2/2000 | Gold | |
| 6,028,186 A | 2/2000 | Tasset | |
| 6,030,776 A | 2/2000 | Eaton | |
| 6,051,698 A | 4/2000 | Janjic | |
| 6,686,158 B2 | 2/2004 | Mandecki | |
| 6,916,661 B2 | 7/2005 | Chandler | |
| 9,127,307 B2 | 9/2015 | Adler, Jr. | |
| 2004/0075907 A1 | 4/2004 | Moon | |
| 2004/0125424 A1 | 7/2004 | Moon | |
| 2004/0126875 A1 | 7/2004 | Putnam | |
| 2004/0130761 A1 | 7/2004 | Moon | |
| 2004/0130786 A1 | 7/2004 | Putnam | |
| 2004/0132205 A1 | 7/2004 | Moon | |
| 2004/0179267 A1 | 9/2004 | Moon | |
| 2007/0036725 A1 | 2/2007 | Bogyo | |
| 2013/0157899 A1* | 6/2013 | Adler, Jr. | C12Q 1/6876 |
| | | | 506/16 |

FOREIGN PATENT DOCUMENTS

| | | |
|---|---|---|
| WO | 2008/057160 | 5/2008 |
| WO | 2008057160 | 5/2008 |
| WO | 2014/108480 | 7/2014 |
| WO | 2014108480 | 7/2014 |

OTHER PUBLICATIONS

Amon, et al, "Integrative proteomic analysis of serum and peritoneal fluids helps identify proteins that are up-regulated in serum of women with ovarian cancer", PLoS One, 5(6) (2010).
Antczak et al., "A Profiling Platform for the Identification of Selective Metalloprotease Inhibitors", J Biomol Screen., 13(4):285-94 (2008).
Blum, et al., "Noninvasive optical imaging of cysteine protease activity using fluorescently quenched activity-based probes", Nat Chem Biol., 3(10):668-77 (2007).
Bregant, et al., "Detection of Matrix Metalloproteinase Active Forms in Complex Proteomes: Evaluation of Affinity versus Photoaffinity Capture", J Proteome Research, 8(5):2484-2494 (2009).
Bulun, "Endometriosis", New England Journal of Medicine, 360:268-279 (2009).
Chan, et al., "Developing Photoactive Affinity Probes for Proteomic Profiling: Hydroxamate-based Probes for Metalloproteases", Journal of the American Chemical Society, 126(44), 14435-46 (2004).
Chen, et al., "Multiplexed Protease Activity Assay for Low-Volume Clinical Samples Using Droplet-Based Microfluidics and its Applications to Endometriosis", Journal of American Chemical Society, 135i, 1645-1648 (2013).
Cho, et al., "Applications of aptamers as sensors", Annu Rev Anal Chem (Palo Alto Calif), 2:241-64 (2009).
Close, "Matrix metalloproteinase inhibitors in rheumatic diseases", Annals of the Rheumatic Diseases, 60 Suppl 3, iii62-7 (2001)/.
Dormán, et al., "The Life of Pi Star: Exploring the Exciting and Forbidden Worlds of the Benzophenone Photophore", Chemical Reviews, 116(24):15284-15398 (2016).
Duncan, et al., "Human matrix metalloproteinase-9: activation by limited trypsin treatment and generation of monoclonal antibodies specific for the activated form", Eur. J Biochem., 258(1):37-43 (1998).
Fulton, et al., "Advanced multiplexed analysis with the FlowMetrix™ system", Clinical Chemistry, American Association for Clinical Chemistry, 43(9):1749-1756 (1997).
Gaide, et al., "Regulation of matrix metalloproteinases activity studied in human endometrium as a paradigm of cyclic tissue breakdown and regeneration", Biochimica et Biophysica Acta, 1824(1):146-56 (2012).
Gygi, et al., "Correlation between protein and mrna abundance in yeast", Mol. Cell. Correlation between protein and mRNA abundance in yeastBiol.19:1720-1730 (1999).
Hai, et al., "In-Capillary Screening of Matrix Metalloproteinase Inhibitors by Electrophoretically Mediated Microanalysis with Fluorescence Detection", Analytical Chemistry, 83(1):425-430 (2011).
Hamaguchi, "Aptamer beacons for the direct detection of proteins", Anal Biochem., 294(2):126-31 (2001).
Hanemaaijer, et al., "A novel and simple immunocapture assay for determination of gelatinase-B (MMP-9) activities in biological fluids: saliva from patients with Sjögren's syndrome contain increased latent and active gelatinase-B levels", Matrix Biology, 17(8-9), 657-65 (1998).
International Search Report for corresponding PCT application PCT/US2018/048231 dated Nov. 2, 2018.
Klein, et al., "Functional proteomics on zinc-dependent metalloproteinases using inhibitor probes", ChemMedChem, 4(2), 164-70 (2009).
Krikun, et al., "A novel immortalized human endometrial stromal cell line with normal progestational response", Endocrinology, 145(5):2291-6 (2004).
Lauer-Fields, et al., "High throughput screening of potentially selective MMP-13 exosite inhibitors utilizing a triple-helical FRET substrate", Bioorganic and Medicinal Chemistry, 17(3):990-1005 (2009).
Laura-Fields, et al., "Development of a Solid-Phase Assay for Analysis of Matrix Metalloproteinase Activity", Journal of Biomolecular Techniques, 15(4), 305-16 (2004).
Li, et al., "Molecular aptamer beacons for real-time protein recognition", Biochem Biophys Res Commun. 292(1):31-40 (2002).

(56) References Cited

OTHER PUBLICATIONS

Miller, et al., "Proteolytic Activity Matrix Analysis (PrAMA) for Simultaneous Determination of Multiple Protease Activities", Integrative Biology, 3(4), 422-38 (2011).

Morales, et al., "Crystal Structures of Novel Non-peptidic, Non-zinc Chelating Inhibitors Bound to MMP-12", J Mol Biol., 341(4):1063-76 (2004).

Naito, et al., "Development of a Neutralizing Antibody Specific for the Active Form of Matrix Metalloproteinase-13", Biochemistry, 51 (44), pp. 8877-8884 (2012).

Nakai, et al., "Ranking the selectivity of PubChem screening hits by activity-based protein profiling: MMP13 as a case study", Bioorganic & Medicinal Chemistry, 17(3): 1101-8 (2009).

Nury, et al., "A Pan Photoaffinity Probe for Detecting Active Forms of Matrix Metalloproteinases", Chembiochem, 14(1):107-14 (2013).

Nuti, et al., "N-O-Isopropyl Sulfonamido-Based Hydroxamates: Design, Synthesis and Biological Evaluation of Selective Matrix Metalloproteinase-13 Inhibitors as Potential Therapeutic Agents for Osteoarthritis", Journal of Medicinal Chemistry, 52(15):4757-4773 (2009).

Rubino, et al., "Direct visualization of serine hydrolase activities in complex proteomes using fluorescent active site-directed probes", Proteomics, 1(9):1067-71 (2011).

Saghatelian, et al., Proceedings of the National Academy of Sciences of the U.S.A., 101(27):10000-5 (2004).

Serdar, et al., "Bifunctional probes of cathepsin protease activity and pH reveal alterations in endolysosomal pH during bacterial infection", Cell Chem Biol, 23(7): 793-804 (2016).

Sieber, et al., "Proteomic profiling of metalloprotease activities with cocktails of active-site probes", Nature Chemical Biology, 2(5):274-81 (2006).

Snoek-Van Beurden, et al., "Zymographic techniques for the analysis of matrix metalloproteinases and their inhibitors", BioTechniques, 38(1), 73-83 (2005).

Sun, et al., "The active form of MMP-3 is a marker of synovial inflammation and cartilage turnover in inflammatory joint diseases", BioMedical, 15:93 1-8 (2014).

Vandenbroucke and Libert, "Is there new hope for therapeutic matrix metalloproteinase inhibition?", Nature Reviews Drug Discovery, 13(12):904-917 (2014).

Chen, et al., "Multiplexed Protease Activity Assay for Low-Volume Clinical Samples Using Droplet-Based Microfluidics and its Application to Endometriosis", *Journal of American Chemical Society*, 135i, 1645-1648 (2013).

\* cited by examiner

- ◖ Active MMP
- ⚬━▶ Activity-based probe (e.g., biotin-tagged hydroxamate benzophenone)
- ◁ Capture antibody
- ) Encoded particle (e.g., color-coded bead)
- ☆ Dye for labeling the probe (e.g., fluorescent streptavidin)

*Laser 1* detects MMP identity based on bead color

*Laser 2* detects MMP amount based on label (dye) intensity

- ◗━▶ Detection (e.g., biotin-tagged) antibody: non-activity based

COMPOSITIONS AND MULTIPLEX ASSAYS FOR CHARACTERIZING ACTIVE PROTEASES AND THEIR INHIBITORS

CROSS-REFERENCED TO RELATED APPLICATIONS

This application claims the benefit of and priority to U.S. Provisional Application No. 62/552,773, filed Aug. 31, 2017 and to U.S. Provisional Application No. 62/585,918, filed Nov. 14, 2017, which are hereby incorporated herein by reference in their entirety.

STATEMENT REGARDING FEDERALLY SPONSORED RESEARCH

This invention was made with Government support under Grant Nos. R01 EB010246 and U54 CA112967 awarded by the National Institutes of Health, and under Grant No. CBET 0939511 awarded by the National Science Foundation. The Government has certain rights in the invention.

FIELD OF THE INVENTION

The invention relates generally to high throughput profiling or screening, and more particularly, relates to detection and characterization of active proteases as well as drug molecules interacting with proteases.

BACKGROUND OF THE INVENTION

Analysis of global changes in gene transcription and translation by systems-based genomics and proteomics approaches provides only indirect information about protein function. In many cases, enzymatic activity fails to correlate with transcription or translation levels (Gygi, S. P, et al., *Mol. Cell. Biol.* 19: 1720-1730 (1999)).

Monitoring and modulating one or two enzymatic activities has failed to deliver therapeutic efficacy, because affected metabolic or signaling pathways are often intertwined with other pathways. "Bypass" signaling occurs where inhibition of one signaling pathway leads to compensatory signaling through alternative routes. For example, metalloproteinase inhibitors including a second-generation inhibitor with specificity toward a disintegrin and metalloproteinases (ADAM) ADAM10 and ADAM17 (INCB7839; Incyte) have failed in clinical trials despite promising initial results (Miller M A, et al., *Cancer Discovery*, 6(4):382-399 (2016)). This can largely be attributed to a poor understanding of how the broad activity of ADAMs, and proteases in general, integrates on a global level to influence overall biological behavior.

Not every translational form of proteins is active. Proproteins are inactive forms that can be converted to an active form by shedding off a piece or adding a molecule. Inhibitors that competitively or non-competitively bind to a protein, particularly an enzyme, directly block the active site or indirectly change the conformation of the enzyme, thereby converting the protein into an inactive form.

For example, while active forms of these enzymes cleave a wide range of extracellular matrix proteins as well as soluble and cell-localized growth factors, cytokines and receptors, metalloproteases are subject to numerous forms of post-translational regulation in vivo, including production as inactive zymogens and inhibition by endogenous proteins (e.g., TIMP, tissue inhibitors of matrix metalloproteinases, and α2-macroglobulin). Elevated pathological protease activities, distinct from total protein levels, are highly correlated with disease states (Chen, et al., *Journal of American Chemical Society*, 135i, 1645-1648 (2013)).

Post-translational events hinder the functional analysis of metalloproteases by conventional, abundance-based genomic and proteomic methods. For example, techniques have been established including zymography (which is performed after the denaturation/renaturation of proteomes, and therefore do not account for key protein-protein or protein-small molecule interactions; Snoek-van Beurden, et al., *BioTechniques*, 38(1), 73-83 (2005)); fluorescence resonance energy transfer (FRET)-based polypeptide cleavage (Miller M, et al., *Integrative Biology*, 3(4), 422-38 (2011)); activity based ELISAs (Hanemaaijer, et al., *Matrix Biology*, 17(8-9), 657-65 (1998); Laura-Fields, et al., *Journal of Biomolecular Techniques*, 15(4), 305-16 (2004)); and active-form specific antibodies or chemical probes (Chan, et al., *Journal of the American Chemical Society*, 126(44), 14435-46 (2004); Sieber, et al., *Nature Chemical Biology*, 2(5), 274-81 (2006); Saghatelian, et al., *Proceedings of the National Academy of Sciences of the U.S.A.*, 101(27): 10000-5 (2004); Antczak, et al., *Journal of Biomolecular Screening*, 13(4):285-94 (2008)).

Existing approaches are limited by the inability to simultaneously measure multiple activities, low throughput, high cost, insensitivity to endogenous inhibitors, as well as incompatibility with direct in situ measurements.

Therefore, it is an object of the present invention to provide reagents and assays for characterizing the activation status or non-inhibited form of a large number of proteins, particularly enzymes or proteases, in a high throughput manner.

It is another object of the present invention to provide reagents and assays for development of therapeutics based on the analysis of the presence, activation state and levels of multiple enzymes, especially proteases.

SUMMARY OF THE INVENTION

Reagents and assays provide sensitive and reliable measurement characterizing the identity and quantification of active proteins in a biological sample in a multiplex manner for a sensitive and reliable measurement based on a low sample volume.

Generally, a sample containing enzymes such as proteases of interest is contacted with an activity-based probe to broadly label active proteins. An identification reagent captures individual proteins regardless of their activation. Simultaneous detection of a signal indicating the presence of activity-based probe and a signal indicating the identification reagent for each probe-labeled and captured protein identifies the presence of an active protein, its identify, and its amount.

Activity-based probes typically possess two or three general elements: (i) a binding group that promotes interaction of the probe with the active sites of enzymes (e.g., proteases), this binding group may also be called as an active-site directed affinity ligand, which may be cross reactive to a number of related enzymes depending on the complexity of the binding group; (ii) a reporter group that is directly detectable or can be labeled with a detectable tag for quantification, and optionally purification, of probe-labeled enzymes; and optionally (iii) a reactive group that covalently bonds the probe to the active enzymes to enhance labeling stability.

An exemplary activity-based probe for labeling active metalloproteases contains a zinc-chelating hydroxamate group for targeting the active site of metalloproteases, optionally a benzophenone photocrosslinking group for covalent bonding with the metalloproteases, and a reporter group such as a biotin.

A spacer or a linker such as a polyalkylene oxide (e.g., polyethylene glycol) may be between the active site binding group and the reporter group to ensure accessibility of the reporter group to secondary detectable labels or detection.

An identification reagent "names" or identifies each enzyme species, regardless of the activation state of the enzyme, therefore regardless of labeling or not labeling by the activity-based probe. Exemplary identification reagent is in the form of encoded particles, for ease of sorting, or a surface in an assay vessel such as multi-well plate, glass slides, or chambers. In preferred embodiments, encoded particles having attached a specific capture reagent or enzyme-identifying molecule are used to capture or immobilize an enzyme species regardless of its activation state. A capture reagent may be an antibody or an aptamer against a protein regardless of the active or inactive form of the protein.

A multiplex reagent set includes a mixture of two or more encoded particle sets encoded such that each particle of each encoded particle set is detectably distinguishable from each particle of each other encoded particle set. Encoding of each particle set is based on one or more properties including optical, chemical, physical, electronic, and magnetic properties. The codes indicate the identity of each encoded particle set. Following incubation of sample with activity-based probes and the encoded particles with an identifying capture reagent, detection of both signals on one encoded particle indicates the identity and quantity of an active protein, protease, or enzyme: a first signal indicating the identity of an encoded particle and a second signal indicating the activity-based probe. In some embodiments, encoded beads are subject to flow cytometry for sorting and detection of the dual signals.

The reagents and assays characterize active proteins, enzymes, or proteases, not their pro-enzyme form or inhibited form, in a panel, yielding results on specific active proteins, enzymes, or proteases, rather than aggregate activity of a general class. A wide range of metalloproteases including MMP1, MMP2, MMP3, MMP7, MMP8, MMP9, MMP10, MMP12, and MMP13 can be tested, unlike other techniques only supporting MMP-2 and 9. The reagents and assays are also compatible with in situ labeling which supports characterization of the in vivo active protease profiles.

Small sample volumes (e.g., about 1, 2, 3, 4, 5, 6, 7, 8, 9, 10 μL) can be measured with high sensitivity (e.g., with a high-level of sensitivity of detection of as low as about 100, 200, 300, 400, 500, 600, 700, 800, 900, 1,000, 1,500, or 2,000 attomoles analyte, 1 attomole=$1\times10^{-18}$ M).

The sensitivity of detection by the reagents and assays can be improved by 10-, 20-, 30-, 40-, 50-, 60-, 70-, 80-, 90-, 100-, 300-, 500-, or 1,000-fold, when a sample is enriched in the concentrations of the active enzymes or proteases compared to detection of a crude biological sample.

The assay requires significantly less sample volume compared to commercially activity-based enzyme-linked immunosorbent assay (requiring 100 μL), and achieves comparable or higher sensitivity.

The reagents and assays for multiplex analysis also allow for simultaneous quantitative measurement of multiple analytes of interest in a single assay to determine candidates for inhibiting the activities of a range of proteins. Such assays are thus suitable for the accumulation of the data required for, and the nature of the samples involved in, the study of proteome, candidate therapeutics, and pathophysiology of a subject.

Biological samples that can be characterized using the reagents and assays include, but are not limited to, living cells or tissues, cultured cells and their media, menstrual fluid, amniotic fluid, peritoneal fluid, serum, plasma, saliva, and urine.

In a preferred embodiment, active enzymes or active proteases are first enriched from a sample, subsequently released from an enrichment carrier under a gentle elution condition, then captured and detectably for identification and quantification as described above. In some embodiments, when a chelating agent such as ethylenediaminetetraacetic acid (EDTA) is used to elute metalloproteinases from an enrichment carrier, the chelating agent is removed before an activity-based probe is added to the sample for identification and quantification of the active metalloproteinases. In other embodiments, when a chelating agent such as EDTA is used to elute metalloproteinases from an enrichment carrier, a biotinylated detection antibody and fluorescent streptavidin are used for identification and quantification of the active metalloproteinases.

Enriching active proteases/enzymes concentrates the active proteases/enzymes and amplifies signals that may otherwise remain below the limit of detection of a reagent set. While a recombinant enzyme sample may contain as little as 1%, or even less, active enzyme, enriching the active enzymes also allows for the preparation of standards (e.g., a calibration curve) to obtain absolute quantities and/or make possible a more absolute comparison of active enzyme concentrations from assay to assay. For example, an enrichment carrier may be magnetic beads with an activity-based probe tethered thereto. Enriched active enzymes may be eluted from the magnetic beads under a mild chelation condition (e.g., use of 10 mM ethylenediaminetetraacetic acid, EDTA, in a suitable buffer), and the enrichment beads tethered with the activity-based probe may be reused.

In some embodiments, the enriched active enzymes/proteases are subsequently identified and quantified with encoded particles. A capture reagent (e.g., antibody or aptamer) may be immobilized on encoded particles. With bound active enzymes/proteases on the capture reagent on the encoded particles, the identity of the bound enzymes/proteases can be detected with detection antibodies (e.g., biotin labeled detection antibody, which is detectable by fluorescent streptavidin). Using a detection antibody further enhances signal amplification (e.g., multiple detection antibodies per immobilized metalloproteinase, or multiple biotins per detection antibody).

Alternatively, the enriched, concentrated active proteases/enzymes are identified and quantified with a capture reagent or an enzyme-identifying molecule which targets the active sites of these proteases/enzymes. Because the active proteases/enzymes are enriched and collected during the enrichment step, in theory without the "impurities" of the inhibited or pro-enzyme form of proteases/enzymes, the identification step can identify and quantify the bound active proteases/enzymes without the need to use an activity-based probe. A capture reagent would suffice, which may be an antibody or an aptamer against a protein (e.g., enzyme/protease) binding to either the active form or the inactive form of the protein.

DETAILED DESCRIPTION OF THE INVENTION

I. Definitions

Figure 1A:
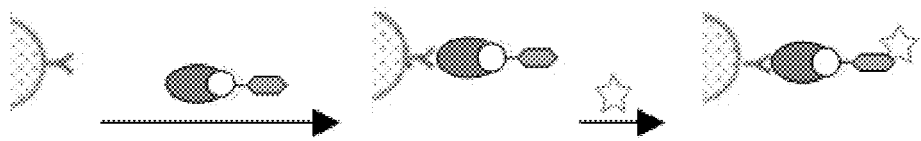
FIG. 1A is a schematic representation of the workflow of the metalloprotease activity multiplexed bead-based immunoassay (MAMBI) platform. In this representation, MAMBI detection requires both the biotin labeling of active proteases and the immuno-capture of labeled proteins. This schematic also represents the general workflow of the reagents and assay of the invention without limiting to metalloproteases. It also applies to the assay for active proteins, active enzymes, and active proteases.

The term "detectable label" refers to any atom or moiety that can provide a detectable signal. Detectable labels are applicable to both labeling the activity-based probes and labeling the protease-identifying encoded beads, though often providing different detectable signal. Examples of detectable labels include fluorescent moieties, chemiluminescent moieties, bioluminescent moieties, ligands, magnetic particles, enzymes, enzyme substrates, radioisotopes and chromophores.

The term "zymogen" or "proenzyme" refers to enzyme precursors that are inactive and can be turned into an active form by post-translational modification such as breaking off a piece or adding another molecule.

The term "derivatives" in one or more relevant contexts include amine, carboxyl, amide, carbonyl, (straight or branched) $C_1$-$C_{20}$ alkyl, aryl (including phenyl, indole), $C(=O)NR_1R_2$ (where $R_1$ denotes hydrogen, alkyl or aryl; and $R_2$ denotes heterocyclic unsaturated or saturated radical having 1 to 4 heteroatoms of elements nitrogen, oxygen, and/or sulfur from the group including furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, tetrazolyl, it being possible for the heterocyclic radical to be substituted once or twice, identically or differently, by halogen, $C_1$~$C_2$-alkyl, $C_1$~$C_4$-alkoxy, $C_1$~$C_4$-alkylthio, hydroxy, mercapto, trifluoromethyl, nitro, phenyl, nitrile, carboxy or $C_1$~$C_4$-alkoxycarbonyl).

II. Reagents, Kit, and Device

Reagents for assaying active enzymes (e.g., proteases, particularly metalloproteases or closely related A disintegrin and metalloproteinases, ADAMs) include (1) molecules as probes that specifically target an activation site or a substrate-binding site of the enzyme, the probe molecules being detectably labeled or capable of being detectably labeled, and (2) a plurality of encoded particles having attached antibodies or other enzyme-identifying molecules for immobilizing and identification of the enzyme.

Generally, the molecules are probes that target an active site of an enzyme and may be cross reactive with active sites of multiple members of a panel of an enzyme family (e.g., depending on the complexity of the active-site targeting molecule, it may be reactive to multiple metalloproteases in a panel). Therefore encoded particles having attached thereto a capture antibody or other molecule capable of identifying a species enzyme is used in conjunction.

The reagents achieve activity-specific measurements by integrating activity-based protein profiling for labeling active sites of an enzyme with multiplex bead array assays for sorting and identifying the enzyme. The assay with these reagents realizes activity-specific measurements in complex biological samples, as well as, multiplexed protein quantification with low sample demands and quick assay time for multiple analytes.

1. Detectably Labeled, Activity-Based Probes

An activity-based probe is a detectably labeled compound targeting an enzyme at its activation or substrate-binding site, and typically possess two or three general elements: (i) a binding group that promotes interaction with the active sites of enzymes (e.g., proteases), also called an active-site directed affinity ligand, which may have cross reactivity to a number of the enzymes dependent on the chemical complexity of the binding group; (ii) a reporter group that is directly detectable or can be labeled with a detectable tag for quantification, and optionally purification, of probe-labeled enzymes; and optionally (iii) a reactive group that covalently labels these active sites, (this element is optional in some embodiments).

Activity-based probes are validated not to cross-react (or not to detectably cross-react) with the pro-form of enzymes or to the TIMP-inhibited form. Suitable activity-based probes for the multiplex assay distinguish from (does not bind to) inactive zymogens and inhibited form of a protease.

In forming a detectably labeled, activity-based probe, any of the active-site binding group below can be combined with any of the reporter group below, optionally including one or more reactive groups for covalently stabilizing the probe with a target enzyme.

a. An Active-Site Binding Group

Any type of active site-targeting molecules may be used in the design of a binding group in an activity-based probe. A small molecule inhibitor, particularly those competitive inhibitors that occupy and block the active site of an enzyme, can be the basis for the active site-binding group of an activity-based probe.

In some embodiments where the target protein is metalloproteases that use a zinc-activated water molecule for catalysis, a general design strategy for the active site binding group is to utilize or incorporate a zinc-chelating hydroxamate group. This binding group also targets other zinc-dependent enzymes, such as zinc-dependent hydrolases including proteases and histone deacetylases. Hydroxamic acid group derivatives are also suitable as the active site-binding element of an activity-based probe for an enzyme.

A broad-spectrum, small molecule, metalloprotease inhibitor may be the chemical basis, or a backbone/scaffold, for designing an activity-based probe targeting metalloproteases. An activity-based probe targeting metalloproteases can be synthesized by modifying the small molecule inhibitors with a reporter group for detection and quantification and optionally a reactive group for triggerable covalent bonding. These small-molecule metalloprotease inhibitors include marimastat, batimastat, Ro 32-3555, ARP 101, ARP 100, UK 370106, TAPI-0, TAPI-1, and TAPI-2. These are commercially available.

In other embodiments where the target enzyme is a serine or cysteine protease (e.g., trypsin, elastase, cathepsins), an active site binding group may be designed to target the conserved nucleophiles in the active sites of these proteases. For example, an activity-based probe that binds to cathepsins generally includes one or more mono-, di-, tri-, or tetra-peptide scaffolds (or containing more amino acids) to impart specificity or selectivity for cathepsin. The peptide scaffold is linked to a fluorophore and to a quencher optionally through a linker (e.g., acyloxymethyl ketone, AOMK). The quencher "masks" or quenches the signal of the fluorophore when situated in close proximity (e.g., on the same peptide scaffold). The fluorophore acts as a reporter group when the quencher is cleaved and leaves the probe. A target protease, cathepsin, cleaves the linker (e.g., at the ester linkage of the AOKM group), forming a probe-enzyme adduct, and separates the quencher from the fluorophore on the probe, thereby generating a signal associated with the probe-enzyme adduct. Exemplary peptide scaffolds include a phenylalanine-lysine dipeptide. Exemplary paired fluorophore and its cognate quencher are sulfo-Cy5 and sulfo-QSY21. Further protease-activity based probes, or their active-site binding groups, are described in U.S. Patent Application Publication No. US 2007/0036725; in *Nat Chem Biol.* 2007, October; 3(10):668-77. Epub 2007 Sep. 9; and in *Cell Chemical Biology* 2016, 23, 793-804. In some embodiments, a pH-dependent, activity-based probe (e.g., containing Oregon Green 488 for fluorescein) replaces or is incorporated into the activity-based probe targeting cysteine proteases, which may be used with a multiplex identification reagent to identify the pH-dependent active protease from a pool of specimens.

A majority of serine hydrolases are potently and irreversibly inhibited by fluorophosphonate/fluorophosphate (FP) derivatives like diisopropyl fluorophosphate, whereas cysteine, aspartyl, and metallohydrolases are for the most part inert to such agents. The reactivity of FPs with serine hydrolases requires that the enzymes be in a catalytically active state. Therefore fluorophosphonate/fluorophosphate (FP) derivatives such as diisopropyl fluorophosphate that are further linked to a reporter group are suitable as a detectably labeled, activity-based probe for labeling active serine hydrolases.

A promiscuous irreversible cysteine protease inhibitor may serve as the chemical basis for devising an activity-based probe for labeling cysteine. Such inhibitor includes the natural product E-64 and derivatives thereof. Modification of these inhibitors with a reporting group and optionally a triggerable covalent binding group provide the probe for the assay. Activity-based probes for labeling cysteine hydrolase superfamily, such as cathepsins and caspases, are further described in Patricelli, M P, et al., *Proteomics*, 1:1067-1071 (2001).

In addition to small molecules, active site targeting antibodies may serve as the binding group of an activity-based probe. Antibodies specific for the active form of a variety of metalloproteases including MMP1 (Millipore MAB3323), MMP-3 (Sun et al., 2014), MMP-7 (Millipore Cat #MAB3322), MMP-9 (Duncan, Richardson, Murray, Melvin, & Fothergill, 1998) and (Millipore Cat #MABT171), and MMP-13 (Naito et al., 2012) are known. A suitable active site targeting antibody for the activity-based probe binds only to uninhibited, active form of a target protein, and therefore does not label the inhibited or non-active form of the target protein.

b. A Reporter Group and Separate, Secondary Detectable Label

A reporter group on the activity-based probe is directly detectable or can be labeled with a detectable tag for quantification, and, optionally, purification, of probe-labeled enzymes.

A reporter group may be the detectable label in an activity-based probe, or it may specifically associate with a secondary detectable label that is separate from the activity-based probe. Exemplary detectable labels include radiolabels, (e.g., $^3$H, $^{14}$C, $^{35}$S, $^{125}$I, $^{131}$I), affinity tags (e.g. biotin/avidin or streptavidin), binding sites for antibodies, metal binding domains, epitope tags, fluorescent or luminescent moieties (e.g. fluorescein and derivatives, green fluorescent protein (GFP), rhodamine and derivatives, lanthanides), colorimetric probe, and enzymatic moieties (e.g. horseradish peroxidase, β-galactosidase, β-lactamase, luciferase, alkaline phosphatase). A detectable label such as biotin, fluorophore-tagged streptavidin, digoxygenin, fluorescein, or cyanine can be selected and introduced to the activity-based probes based on the association interaction between a detectable label and an activity-based probe.

In one embodiment the activity-based probe contains biotin as a reporter group; and in another embodiment, streptavidin conjugated to a fluorescent or illuminescent group, such as streptavidin-phycoerythrin (a red fluorescent label), is further added to the activity-based probe labeling an enzyme to facilitate detection and quantification.

c. A Reactive Group for Stabilizing the Binding with Target Protein

Optionally, an activity-based probe for labeling the active site of an enzyme includes an element (or a group) that promotes selective covalent binding to the enzyme. As many active site-directed binding groups associate with the active site of an enzyme based on chelation, electrostatic interaction, or hydrophobic-hydrophilic interactions, a covalent binding between an activity-based probe and the targeted enzyme increases the stability of the probe-labeled enzyme and may enhance the robustness of the multiplex assay.

Generally a reactive group in an activity-based probe allows spontaneous or triggerable bonding with the enzyme of interest, and the covalent bonding does not interfere with the reading of the multiplex assay to a detectable extent.

Some embodiments provide a benzophenone photocrosslinking group as part of the activity-based probe to promote selective binding and covalent modification of the active sites of a target protein such as metalloprotease.

Other photoactivatable groups suitable for inclusion in the activity-based probe to crosslink it to an enzyme of interest include an aryl azide group such as bimane azide, fluorinated aryl azide group.

d. Linker/Spacer

An activity-based probe for labeling the active site of an enzyme may include a spacer between the active site-binding group and the reporter group. This is to allow the reporter group to be accessible for detection or for secondary detectable labels to bind thereto. Suitable spacers or linkers include polyethylene glycol, polyalkylene glycol, which may be of a molecular weight between 50 and 100,000 Da.

Exemplary detectably labeled, activity-based probes are shown in Formulae 1, 12, and 13 in the Examples. Also suitable are derivatives thereof which replace one or more hydrogens with amine, carboxyl, amide, carbonyl, (straight or branched) $C_1$-$C_{20}$ alkyl, aryl (including phenyl, indole), $C(=O)NR_1R_2$ (where $R_1$ denotes hydrogen, alkyl or aryl; and $R_2$ denotes heterocyclic unsaturated or saturated radical having 1 to 4 heteroatoms of elements nitrogen, oxygen, and/or sulfur from the group including furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, tetrazolyl, it being possible for the heterocyclic radical to be substituted once or twice, identically or differently, by halogen, $C_1$~$C_2$-alkyl, $C_1$~$C_4$-alkoxy, $C_1$~$C_4$-alkylthio, hydroxy, mercapto, trifluoromethyl, nitro, phenyl, nitrile, carboxy or $C_1$~$C_4$-alkoxycarbonyl).

2. Multiplex Identification Reagent

While the activity-based probe may label a panel of enzymes due to its cross reactivity to active sites on different enzymes, an identification reagent to "name" each enzyme species allows for identification of each of the active enzymes. The identification reagent may be in the form of particles, for ease of sorting, or in the form of a surface in an assay vessel such as the multiwell plate, glass slides, or chambers.

Generally, each set of encoded particles or each well has bound thereto one type of capture reagent or enzyme-identifying molecules so as to identify a single species or a single class of proteases. A multiplex reagent includes a mixture of two or more encoded particle sets encoded such that each particle of each encoded particle set is detectably distinguishable from each particle of each other encoded particle set.

a. Encoded Particles

Particles to which capture antibodies or other protease-identifying biomolecules are bound can be any solid or semi-solid particles to which a protease-identifying biomolecule can be attached, which are suitable for a multiplex assay and which are stable and insoluble under protease detection conditions. The particles can be of any shape, such as cylindrical, spherical, or irregular, size, composition, or physiochemical characteristics. The particle size or composition can be chosen so that the particle can be separated from fluid, e.g., on a filter with a particular pore size or by some other physical property, e.g., a magnetic property.

An exemplary type of particles is microparticles, such as microbeads, which can have a diameter of less than one millimeter, for example, a size ranging from about 0.1 to about 1,000 micrometers in diameter, inclusive, such as about 3-25 microns in diameter, inclusive, or about 5-10 microns in diameter, inclusive. Another exemplary type of particles are nanoparticles, such as nanobeads, which can have a diameter from about 1 nanometer (nm) to about 100,000 nm in diameter, inclusive, for example, a size ranging from about 10-1,000 nm, inclusive, or for example, a size ranging from 200-500 nm, inclusive. In certain embodiments, particles are beads (spherical or about spherical shaped), particularly microbeads and nanobeads.

Particles can be organic or inorganic particles, such as glass or metal, or formed of a synthetic or naturally occurring polymer, such as polystyrene, polycarbonate, silicon, nylon, cellulose, agarose, dextran, and polyacrylamide. Particles are latex beads in particular embodiments.

Particles include functional groups for binding to capture antibodies or other protease-identifying biomolecules in particular embodiments. For example, particles can include carboxyl, amine, amino, carboxylate, halide, ester, alcohol, carbamide, aldehyde, chloromethyl, sulfur oxide, nitrogen oxide, epoxy and/or tosyl functional groups. Functional groups present on or which can be attached to particles, modification thereof and binding of a chemical moiety, such as an antibody, thereto are known in the art, for example, as described in Fitch, R. M., Polymer Colloids: A Comprehensive Introduction, Academic Press, 1997. In a further particular example, 1-Ethyl-3-[3-dimethylaminopropyl]carbodiimide hydrochloride, EDC or EDAC chemistry, can be used to attach capture antibodies or protease identifying molecules to encoded particles.

Particle Encoding (Multiplexed Assay)

Particles are encoded or indexed, such that each set of encoded particles are distinguishable from other particles based on a characteristic illustratively including an optical property such as color or reflective index, magnetic index, and/or an imprinted or otherwise optically detectable pattern, i.e., a system that is multiplexed. For example, the particles may be encoded using optical, chemical, physical, electronic, or magnetic tags. Encoded particles can contain or be attached to, one or more fluorophores which are distinguishable, for instance, by excitation and/or emission wavelength, emission intensity, excited state lifetime or a combination of these or other optical characteristics. Optical bar codes can be used to encode particles.

In particular embodiments, each particle of a particle set is encoded with the same code such that each particle of a particle set is distinguishable from each particle of another particle set. In further embodiments, two or more codes can be used for a single particle set. Each particle can include a unique code, for example. In certain embodiments, particles encoding includes a code other than or in addition to the association of a particle and a capture antibody or protease-identifying molecule.

In particular embodiments, the code is embedded, for example, within the interior of the particle, or is otherwise attached to the particle in a manner that is stable through hybridization and analysis. The code can be provided by any detectable means, such as by holographic encoding, by a fluorescence property, color, shape, size, light emission, or quantum dot emission to identify particle and thus the capture antibodies or protease-identifying molecules immobilized thereto.

One exemplary platform utilizes mixtures of fluorescent dyes impregnated into polymer particles as the means to identify each member of a particle set to which a specific capture probe has been immobilized. Another exemplary platform uses holographic barcodes to identify cylindrical glass particles. For example, U.S. Pat. No. 5,981,180 to Chandler describes a particle-based system in which different particle types are encoded by mixtures of various proportions of two or more fluorescent dyes impregnated into polymer particles. U.S. Pat. No. 5,028,545 to Soini describes a particle-based multiplexed assay system that employs time-resolved fluorescence for particle identification. U.S. Pat. No. 4,499,052 to Fulwyler describes an exemplary method for using particle distinguished by color and/or size. U.S. Patent Application Publications 20040179267, 20040132205, 20040130786, 20040130761, 20040126875, 20040125424, and 20040075907 describe exemplary particles encoded by holographic barcodes. U.S. Pat. No. 6,916,661 describes polymeric microparticles that are associated with nanoparticles that have dyes that provide a code for the particles.

An exemplary embodiment utilizes the LUMINEX® encoded bead platform. Other types of encoded particle assay platforms may be used, such as the VERACODE® beads and BEADXPRESS® system (Illumina Inc., San Diego Calif.), and xMAP 3D® (Luminex). Magnetic LUMINEX® beads can be used which allow wash steps to be performed with plate magnets and pipetting rather than with filter plates and a vacuum manifold. Each of these platforms are typically provided as carboxyl beads but may also be configured to include a different coupling chemistry, such as amino-silane.

Single-plexed detection systems can also be used, where one encoded particle set is provided to contact samples.

b. Capture Reagents or Enzyme-Identifying Molecules

A capture reagent is used to "capture" or immobilize a specific type or species of enzyme, regardless of the enzyme activity (pro-enzyme, active enzyme, or inhibited enzyme). Couple with the unique coding identifier of the encoded particles, the capture reagent on uniquely coded particles (also denoted as enzyme-identifying molecule) "names" or identifies a specific, bound enzyme. In preferred embodiments, the capture reagents are antibodies, such as monoclonal antibodies, aptamers such as nucleic acid or peptide aptamers, and other types of proteins such as knottins and FN3 mutants.

Antibodies

Antibodies that can be used in the compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Fragments of antibodies which have bioactivity can also be used. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Suitable antibodies as the capture reagents on encoded particles for immobilizing enzymes may be commercially available. These capture antibodies need not distinguish between pro- and active form of an enzyme of interest. For example, antibodies that specifically bind MMP9 (ABCAM® #ab38898), MMP2 (pro- and active) (NOVUS BIOLOGICALS® #NB200), morphine (Abcam® #ab1060, #ab23357), MMP3 (ABCAM® #ab52915), MMP1 (ABCAM® #ab52631), MMP7 (ABCAM® #ab5706), and MMP12 (ABCAM® #ab52897), are commercially available.

Antibodies that specifically bind an enzyme can also be made using routine methods. For example, antibodies can be purified from animals immunized with the enzyme. Monoclonal antibodies can be produced by fusing myeloma cells with the spleen cells from a mouse that has been immunized with the opioid analyte or with lymphocytes that were immunized in vitro. Antibodies can also be produced using recombinant technology.

Nucleic Acid Aptamers

Nucleic acid aptamers are typically oligonucleotides ranging from 15-50 bases in length that fold into defined secondary and tertiary structures, such as stem-loops or G-quartets. The oligonucleotide may be DNA or RNA, and may be modified for stability. A nucleic acid aptamer generally has higher specificity and affinity to a target molecule than an antibody. Nucleic acid aptamers preferably bind the target molecule with a $K_d$ less than $10^{-6}$, $10^{-8}$, $10^{-10}$, or $10^{-12}$. Nucleic acid aptamers can also bind the target molecule with a very high degree of specificity. It is preferred that the nucleic acid aptamers have a $K_d$ with the target molecule at least 10, 100, 1000, 10,000, or 100,000 fold lower than the $K_d$ with other molecules. In addition, the number of target amino acid residues necessary for aptamer binding may be smaller than that of an antibody.

Nucleic acid aptamers are typically isolated from complex libraries of synthetic oligonucleotides by an iterative process of adsorption, recovery and reamplification. For example, nucleic acid aptamers may be prepared using the SELEX (Systematic Evolution of Ligands by Exponential Enrichment) method. The SELEX method involves selecting an RNA molecule bound to a target molecule from an RNA pool composed of RNA molecules each having random sequence regions and primer-binding regions at both ends thereof, amplifying the recovered RNA molecule via RT-PCR, performing transcription using the obtained cDNA molecule as a template, and using the resultant as an RNA pool for the subsequent procedure. Such procedure is repeated several times to several tens of times to select RNA with a stronger ability to bind to a target molecule. The base sequence lengths of the random sequence region and the primer binding region are not particularly limited. In general, the random sequence region contains about 20 to 80 bases and the primer binding region contains about 15 to 40 bases. Specificity to a target molecule may be enhanced by prospectively mixing molecules similar to the target molecule with RNA pools and using a pool containing RNA molecules that did not bind to the molecule of interest. An RNA molecule that was obtained as a final product by such technique is used as an RNA aptamer. Representative examples of how to make and use aptamers to bind a variety of different target molecules can be found in U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698. An aptamer database containing comprehensive sequence information on aptamers and unnatural ribozymes that have been generated by in vitro selection methods is available at aptamer.icmb.utexas.edu.

In some embodiments, the aptamer is a molecular aptamer beacon. A molecular beacon is a hairpin-shaped oligonucleotide with a fluorophore and a quencher linked to each end of its stem. The signal transduction mechanism for molecular recognition is based on resonance fluorescence energy transfer (FRET) and the conformational change of a molecular beacon. The molecular beacon acts like a switch that is normally closed to bring the fluorophore/quencher pair together to turn fluorescence "off". When binding to a target biomolecule, it undergoes a conformational change that opens the hairpin structure and separates the fluorophore and the quencher, thus turning "on" the fluorescence. Molecular aptamer beacons were developed to combine the sequence specificity and sensitivity of aptamers with the real-time detection advantages of molecular beacons. Briefly, oligonucleotides containing a nucleic acid aptamer sequence are designed to have complementary DNA or RNA sequences that form a hairpin, which is opened when the aptamer sequence binds its target. Molecular aptamer beacons are described in Cho et al. *Annu Rev Anal Chem (Palo Alto Calif.)* 2:241-64 (2009), Hamaguchi N, et al. Anal Biochem. 294(2):126-31 (2001); Li J J, et al. *Biochem Biophys Res Commun.* 292(1):31-40 (2002).

Peptide Aptamers

Peptide aptamers are small peptides with a randomized amino acid sequence that are selected for their ability to bind a target molecule such as an enzyme. Peptide aptamer selection can be made using different systems, but the most used is currently the yeast two-hybrid system. Peptide aptamer can also be selected from combinatorial peptide libraries constructed by phage display and other surface display technologies such as mRNA display, ribosome display, bacterial display and yeast display. These experimental procedures are also known as biopannings. Among peptides obtained from biopannings, mimotopes can be considered as a kind of peptide aptamers. All the peptides panned from combinatorial peptide libraries have been stored in a special database, MimoDB.

3. Optional Enrichment Reagents

In some embodiments where the concentration of active enzyme/protease is low or below the detection limit of the activity-based probes, a sample may undergo an enrichment process where active enzymes or active proteases are isolated and separated from the rest of the sample (e.g., from pro-enzyme form or inhibited form of enzyme/protease), thus concentrated. The reagents for this enrichment step generally include (1) an activity-based probe for active enzyme enrichment, (2) an enrichment carrier that is facilely retrievable from a surrounding medium, and optionally (3) an elution agent to release active enzyme/protease from the activity-based probe used in the enrichment step.

An activity-based probe for active enzyme enrichment may be a compound or molecule having an active-site binding group and a "tag" that allows for the association or recognition for association with an enrichment carrier.

For example, the active-site binding group of the activity-based probe for active enzyme enrichment may be based on a small-molecule competitive inhibitor that occupies and blocks the active site of an enzyme/protease. It may also be any of those active-site binding group described above in relation to activity-based probes (e.g., hydroxamate-based inhibitors that bind to zinc-dependent enzymes).

The "tag" to associate with or for recognition for association with an enrichment carrier may be an affinity group, and is selected in pair with the enrichment carrier. For example, the tag may be a biotin molecule, and it is covalently conjugated with the active-site binding group. For instance, sulfosuccinimidobiotin (Biotin-NHS) may be covalently conjugated with hydroxamate based inhibitors, TAPI-0, TAPI-1, or TAPI-2, via the free primary amine group on them. Paired with the biotin-tagged activity-based probe for active enzyme enrichment, a biotin-binding enrichment carrier is preferred such as magnetic biotin-binding beads.

An enrichment carrier is generally any solid or semi-solid particles to which an activity-based probe for active enzyme enrichment may associate to and which may be retrieved from a surrounding medium via a physical property or other properties. The particles can be of any shape, such as cylindrical, spherical, or irregular, size, composition, or physiochemical characteristics. The particle size or composition can be chosen so that the particle can be retrieved from a surrounding medium or separated from fluid, e.g., on a filter with a particular pore size or by some other physical property, e.g., a magnetic property. In some embodiments, the enrichment carrier is a superparamagnetic particle, which is additionally modified for association with the activity-based probe for active enzyme enrichment via the "tag". Exemplary superparamagnetic particles include superparamagnetic metal oxide nanodots, e.g., superparamagnetic iron oxide nanodots. In the embodiments where the activity-based probe for active enzyme enrichment includes a biotin as a "tag", an enrichment carrier is generally streptavidin-coupled superparamagnetic particles, e.g., streptavidin-coupled DYNABEADS® and MAGNA-LINK™ streptavidin magnetic beads; or avidin-coupled superparamagnetic particles.

An elution agent releases the active enzyme/protease from the activity-based probe. For example, the elution agent may be a buffered aqueous solution containing ethylenediaminetetraacetic acid (EDTA) from about 0.1 mM to about 500 mM, more preferably between about 5 mM and 100 mM, or about 10 mM. A wash buffer (e.g., PBS/T) is used to wash away unbound proteins at first, and then an EDTA supplemented buffer releases the bound, active enzyme/protease from the activity-based probe.

4. Kit for Assays

Kits for assaying active proteins, enzymes, or proteases are provided. The reagents may be assembled in a kit generally containing one or more, or all, of the following components (some may be combined): an activity-based probe, diluent for the activity-based probe, a secondary detectable label for labeling the activity-based probe, diluent for the dye for labeling the activity-based probe, microparticles or color-coded beads, diluent for the microparticles or the color-coded beads, capture antibodies or identification components, diluent for the capture antibodies or the identification components, wash buffer or wash buffer concentrate; as well as other components such as mixing bottles or vials, a vessel for the assay (e.g., multiwell microplate), plate sealer (adhesive foil strips), calibration standards (e.g., active protein of known concentration, diluent), and an instruction manual.

In particular embodiments, a kit is provided which includes an encoded particle set and/or a mixture of two or more encoded particle sets having bound a capture antibody or protease-identifying molecule, as well as detectably labeled activity-based probes specifically targeting the active site of proteases. Instructional material for use of the assay reagents optionally included in a kit. An ancillary reagent such as buffers, enzymes, washing solutions, hybridization solutions, detectable labels, detection reagents and the like are also optionally included.

One or more of the above mentioned diluents may also contain buffering agents and/or preservatives.

5. Wearable Device and Point-of-Care Assay

The reagents for assaying active proteins may be situated in a device that is wearable by a subject. The device may additional includes a receiver that allows collection of a body fluid as sample from a subject, a processer for assaying sample with the reagents, and a detector that measures the identity and amount or relative amount of active proteins (e.g., active proteases) in the sample.

A rapid, reliable, sensitive, qualitative, and quantitative point-of-care assay is provided with the reagents above to quantitatively measure active protease profiles in a biological sample from a subject or a patient, including human and veterinary subjects. The point-of-care assay can also quantitatively measure analytes of interest that may inhibit or interfere with the activity of proteases or the proteolytic profiles of a biological sample.

Some embodiments provide a means for communicating data collected from or instructions for using the multiplex assay for one or more of (1) assaying protease in its active form from a sample, (2) screening for drugs inhibiting protease, or (3) assessing the health status of a subject. The means includes a document, digital storage media, optical storage media, audio presentation, or visual display containing the information or instructions. In certain embodiments, the communication means is a displayed web site, visual display kiosk, brochure, product label, package insert, advertisement, handout, public announcement, audiotape, videotape, DVD, CD-ROM, computer readable chip, computer readable card, computer readable disk, computer memory, or combination thereof containing such information or instructions.

III. Assay Method

The assay performs well with as little as 1, 2, 3, 4, or 5 μL of sample fluid, with a high-level of sensitivity of detection of as low as about 100, 200, 300, 400, 500, 600, 700, 800, 900, 1,000, 1,500, or 2,000 attomoles (1 attomole=$1\times10^{-18}$ M).

Assays can be performed in any suitable container.

In particular embodiments, encoded particles are evaluated individually. For example, the particles can be passed through a flow cytometer. Exemplary flow cytometers include the Coulter Elite-ESP flow cytometer, or FACScan™ flow cytometer available from Beckman Coulter, Inc. (Fullerton Calif.) and the MOFLO™ flow cytometer available from Cytomation, Inc., Fort Collins, Colo. In addition to flow cytometry, a centrifuge may be used as the instrument to separate and classify the particles. A suitable system is that described in U.S. Pat. No. 5,926,387. In addition to flow cytometry and centrifugation, a free-flow electrophoresis apparatus may be used as the instrument to separate and classify the particles. A suitable system is that described in U.S. Pat. No. 4,310,408. The particles may also be placed on a surface and scanned or imaged.

Other embodiments use a multi-chamber container for assaying multiple samples. Multi-chamber containers illustratively include multi-depression substrates such as slides, silicon chips or trays. In some embodiments, each sample is disposed in a different well of a multi-well plate such as a 96-well, 384-well, or 1024-well assay plate.

Other embodiments provide detection of both the activity-based probe signal and the identification reagent signal based on fluorescence changes or chemical reactions due to the physical proximity between the activity-based probe and the identification reagent when an active enzyme is probed and captured. Fluorescence resonance energy transfer (FRET) between the probe and the identification reagent may provide a detection signal, where excitation of a chromophore on the probe or on the identification reagent leads to activation of another chromophore on the capture reagent or the probe, respectively. Proximity ligation assays (PLA) provides another detection signal, where one part for the PLA is on the active-based label and the other part is on the identification reagent.

Workflow

An exemplary workflow of the assay is as follows. Analyte-specific antibodies ("capture antibody" in FIG. 1A) or other identification components, (not required to target the active site of an analyte) are pre-coated onto color-coded magnetic microparticles ("color-coded bead" in FIG. 1A). Microparticles and samples are pipetted together and the immobilized antibodies bind the analytes of interest. After washing away any unbound substances, an activity-based probe (e.g., HxBP-Bt for labeling zinc-dependent metalloproteases at their active sites) is added. Following a wash to remove any unbound activity-based probes, a dye for labeling the probe (e.g., streptavidin-phycoerythrin conjugate for activity-based probes containing biotin as a reporter group) is added. A final wash removes unbound dye, and the microparticles are resuspended in buffer and read using an analyzer.

Figure 1B:
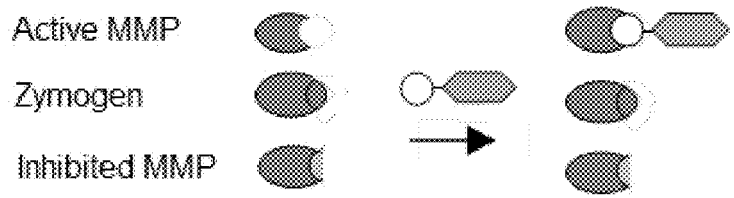
FIG. 1B is a schematic representation of an activity-based probe selectively binds to active MMP, rather than the zymogen form or the inhibited MMP.
Figure 1C:
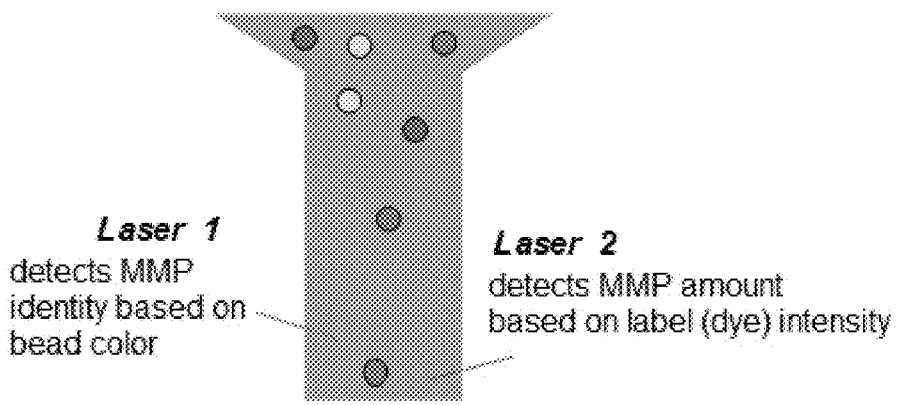
FIG. 1C is a schematic representation of the laser detection system of the MAMBI platform, in which one laser detects the identity of MMP based on the color code of the bead with a known capture antibody for a particular MMP and another laser detects the amount of MMP on such bead based on the intensity of a chromophore dye that binds to or labels the activity-based probe.

One form of an analyzer is a sorting and detection platform as shown in FIG. 1C to analyze the analyte-bound microparticles rapidly. Exemplary sorting and detection platforms include LUMINEX® 100/200 or Bio-Rad Bio-Plex dual laser, flow-based systems. One laser identifies the analyte that is being detected, based on the color code of the microparticles, and the second laser determines the magnitude of the dye signal, which is in direct proportion to the amount of analyte bound.

Alternatively, the analyzer is a detection and imaging platform, such as the Luminex MAGPIX Analyzer. Generally, a magnet in the analyzer captures and holds the superparamagnetic microparticles in a monolayer. Two spectrally distinct Light Emitting Diodes (LEDs) illuminate the beads. One LED identifies the analyte that is being detected, based on the color code of the microparticles, and the second LED determines the magnitude of the dye signal, which is in direct proportion to the amount of analyte bound. This workflow is compatible with well plate-based assays where the samples and MAMBI reagents are prepared in wells. Each well is imaged with a CCD camera upon LED illumination.

Another exemplary workflow of the MAMBI system differs in the order of reagent incubation of the analytes. For example, an activity-based probe is incubated with the samples first. Color coded beads are later added to the incubated samples. Following one or more washes to remove unbound activity-based probe, a dye for labeling the probe is added. A final wash removes unbound dye, and the beads are read using an analyzer.

The activity-based probe should not bind directly to the color-coded bead or the capture antibody thereon. Otherwise, a control lacking the analyte of interest (e.g., the protein samples) should be included to subtract its signal from the one tested with the analyte of interest in the MAMBY system.

Figure 17:
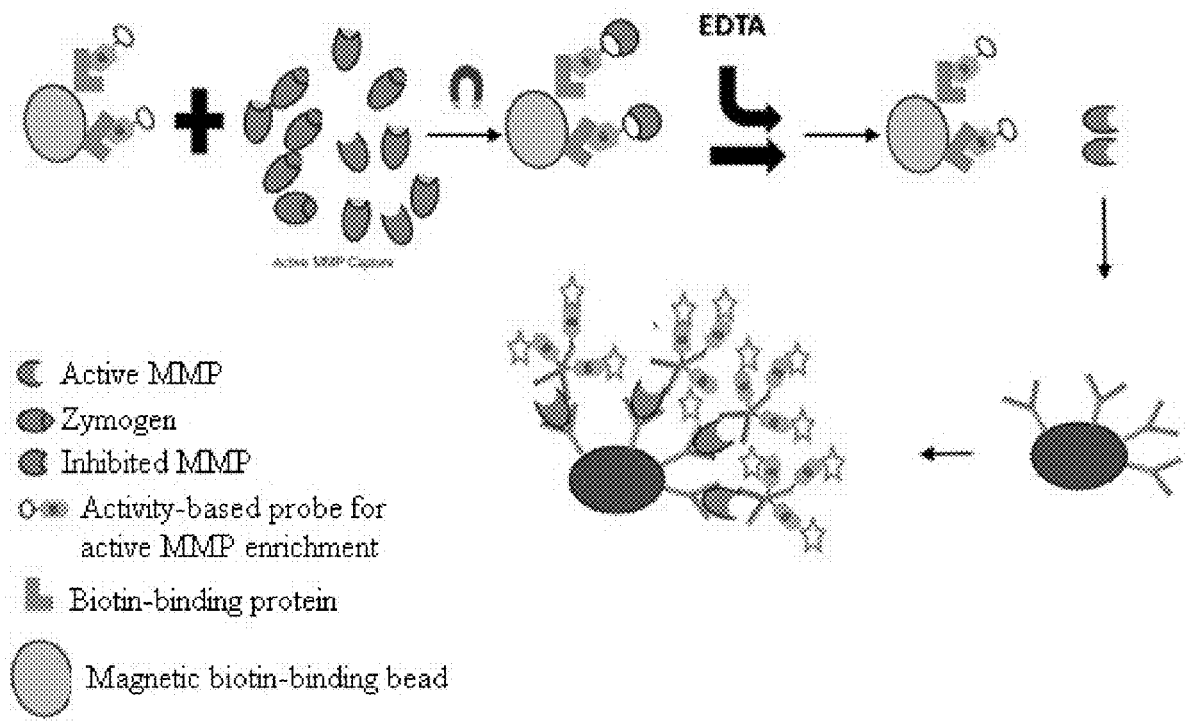
FIG. 17 is a diagram showing the enrichment of active MMPs prior to identification and quantification in an assay.

Another exemplary workflow of the assay begins with enrichment of active proteases/enzymes. FIG. 17 shows a schematic workflow of enrichment and release of active MMPs. An activity-based probe containing a biotin as a "tag" is associated with the magnet beads, and the beads are coated with one or more biotin-binding proteins (e.g. streptavidin, avidin). The magnetic bead with the bound activity-based probe is then incubated with a mixture of inactive and active MMPs. Inactive MMPs are removed by placing beads under magnetic field and washing. Active MMPs are then eluted from the beads with 10 mM EDTA in wash buffer. The elution fraction is then incubated with encoded particles coated with specific capture reagents (e.g. antibodies), then subsequently detected with biotin labeled antibodies and fluorescent streptavidin.

IV. Use of Reagents and Assay

1. Assay Active Protein Profiles from Biological Samples

The reagents and assays are suitable for characterizing the profile of active proteins in a biological samples, particularly distinguishing over reagents and assays for protein profiles regardless of the activity of the proteins.

The reagent and assay apply to determining active protein profiles for various types of proteins such as enzymes, growth factors, and other hormones such as insulin and piomelanocortin, including active, inactive and precursor proteins. A protein precursor, also called a pro-protein or pro-peptide, is an inactive protein (or peptide) that can be turned into an active form by post-translational modification, such as breaking off a piece of the molecule or adding on another molecule.

Enzymes generally have a pro-enzyme form which is inactive, an inhibited form where the active site is blocked or occupied, and an active form where the active site is available for carrying out of enzymatic reactions.

Exemplary enzymes suitable for characterization on their active form profiles include oxidoredectases, transferases, hydrolases, lyases, isomerases, and ligases. Particularly, proteases are characterized for the active form profiles to assess the health or pathological conditions of a subject. Exemplary proteases include serine proteases, cysteine proteases, threonine proteases, aspartic proteases, glutamic proteases, metalloproteases, and asparagine peptide lyases.

Matrix Metalloproteinases (MMPs)

MMPs include 24 known human zinc proteases with essential roles in breaking down components of the extracellular matrix (ECM). In addition to ECM proteins, other potential MMP substrates include cytokines, chemokines, growth factors and binding proteins, cell/cell adhesion molecules, and other proteinases. With a few exceptions, MMPs share common structural motifs including a pro-peptide domain, a catalytic domain, a hinge region, and a hemopexin-like domain. Synthesized as pro-enzymes, most are secreted before conversion to their active forms. In general, the activation mechanism is thought to occur in a stepwise fashion involving disruption of the interaction between the catalytic site zinc and a cysteine-thiol group in the pro-peptide domain. This is followed by cleavage of the pro-peptide. Activation can be mediated by several serine proteases, MMPs, or potentially via NO-mediated S-nitrosylation of the pro-peptide cysteine-thiol group. In some cases, activation can take place intracellularly via a furin-like serine protease. MMPs are expressed by many cell types and can be upregulated in response to adhesion molecules, growth factors, cytokines, and hormones. They have been implicated in several physiological processes including tissue morphogenesis, cell migration, wound healing, bone remodeling, and angiogenesis.

ADAMs (a Disintegrin and Metalloproteinase)

The ADAMs family of transmembrane proteins belongs to the zinc protease superfamily. Members of the family have a modular design, characterized by the presence of both metalloprotease and integrin receptor-binding activities, and a cytoplasmic domain that in many family members specifies binding sites for various signal transducing proteins. The ADAMs family has been implicated in the control of membrane fusion, cytokine and growth factor shedding, and cell migration, as well as processes such as muscle development, fertilization, and cell fate determination. Pathologies such as inflammation and cancer also involve ADAMs family members. In humans, there are 19 adam genes. ADAMs are found in vertebrates, as well as in *Caenorhabditis elegans, Drosophila,* and *Xenopus.*

Cathepsins

Cathepsins are proteases found in all animals as well as other organisms, whose activities are optimal at lysosomal acidic and reducing conditions, significantly contributing to the degradation of the extracellular matrix. Cathepsins are a group of lysosomal proteases that have a key role in cellular protein turnover. The term cathepsin includes serine proteases, aspartic proteases, and cysteine proteases. Most cathepsins are endopeptidases, with the exception of cathepsin C and Z. All cysteine cathepsins are expressed as polypeptides consisting of a signal sequence, a propeptide, and a catalytic domain.

Complex biological samples are well characterized by the reagents and assays using a small volume for high sensitivity detection of active proteins.

Exemplary sources of the samples include whole proteomes, living cells or tissues, cultured cells, and body fluids such as menstrual fluid, amniotic fluid, peritoneal fluid, serum, plasma, saliva, and urine.

Serum

With serum samples, a serum separator tube (SST) may be used to allow samples to clot for a period of time (e.g., 30 minutes at room temperature) before centrifuging (e.g., for 15 minutes at 1000×g). The clear portion is assayed immediately or aliquot and store samples at ≤−20° C. Avoid repeated freeze-thaw cycles.

Plasma (or Platelet-Poor Plasma)

With plasma samples, generally plasma is collected using heparin as an anticoagulant and centrifuge within 30 minutes of collection (e.g., for 15 minutes at 1000×g). The fluid portion is assayed immediately or aliquot and store at ≤−20° C. Repeated freeze-thaw cycling is generally avoided.

Some MMPs may be released upon platelet activation. Platelet-poor plasma should be used for these analytes. Incomplete removal of platelets or platelet activation may cause variable and irreproducible results for assays of factors contained in platelets and released by platelet activation. For platelet removal, the separated plasma may be centrifuged of at 10,000×g for 10 minutes at 2-8° C.

Saliva

With saliva samples, generally saliva is collected in a sterile container and centrifuged (e.g., for 5 minutes at 10,000×g). The aqueous layer is assayed immediately or aliquot and store at ≤−20° C. Repeated freeze-thaw cycling is generally avoided.

Urine

With urine samples, generally the urine is aseptically collected in a sterile container. Centrifugation removes particulate matter, and the fluid portion is assayed immediately or aliquot and store at ≤−20° C. Repeated freeze-thaw cycling is generally avoided.

While methods and compositions are described primarily with reference to proteases present in or obtained from humans, it is appreciated that methods and compositions may be used to assay proteomic samples from any of various organisms including, but not limited to, non-human primates, rodents, rabbits, dogs, cats, horses, cattle, pigs, goats, and sheep. Non-mammalian sources can also be assayed, illustratively including fish and other aquatic organisms, birds, poultry, bacteria, viruses, plants, insects, reptiles, amphibians, fungi and mycobacteria.

2. Drug Discovery

The reagents and assays can also be used for screening therapeutics/drugs that inhibits, interfere, and/or competitively bind to the active site of proteins. These drugs competitively bind to the active site of the proteins, thereby decreasing the association between the activity-based probe and the protein. Analyzing the reduction in the signal of probe-labeled protein compared to that detected in the absence of a candidate analyte provides information on the inhibition potency, or the association potency, of the candidate analyte with the protein.

Exemplary analytes are molecules for potential inhibition of proteases. Activity-based probes with a relatively lower labeling potency (lower association ability) of the protease may be used to identify a relatively large number of competitive binding candidate analytes.

The multiplex system also allows for screening candidate inhibitors for each of many proteases.

3. Point-of-Care

The reagents and assay to characterize active proteins may be situated in a device that supports point of care to a subject. The device may be wearable and additional include a receiver that allows collection of a body fluid as sample from a subject, a processer for assaying sample with the reagents, and a detector that measures the identity and amount or relative amount of active proteins (e.g., active proteases) in the sample. The device measures active protease profiles in a biological sample from a subject or a patient, and can also quantitatively measure analytes of interest that may inhibit or interfere with the activity of proteases or the proteolytic profiles of a biological sample.

The reagents and assays facilitates assessment of health conditions of a subject by diagnosing and/or monitoring the active protein profiles (level and identity), particularly active protease profiles which may be highly associated with tumor progression, aggressive tissue remodeling, neurodegenerative disorders, inflammatory diseases, and cardiovascular diseases, among other diseases and disorders. In some embodiments, patients with endometriosis and preeclampsia are assessed in their body fluid for the active protease profiles before, during, and/or after a treatment.

*Seminars in Reproductive Medicine*, (2003)) (Gaide Chevronnay et al., *Biochimica et Biophysica Acta,* 1824(1), 146-56 (2012)), whereas dysregulated MMP activity has been associated with pathologies such as endometriosis (Serdar bulun, *New England Journal of Medicine,* 360:268-279 (2009)) and preeclampsia. The relative MMP activity was quantified in cell culture supernatant, peritoneal fluid aspirates, and menstrual serum effluent. The MAMBI technique was further used in screening relative potency and selectivity of a panel of small molecule inhibitors of MMPs.

Example 1. Validation of MAMBI Selectivity for Quantifying Active MMPs

Materials

Recombinant human enzymes MMPs 1, 2 and 3 and TIMP2 were purchased from Peprotech. The recombinant catalytic domains of human MMPs 7 and 9 were purchased from Enzo Life Sciences, and of MMP 12 from Anaspec. FRET-substrates were purchased from BioZyme, Inc. Streptavidin-R-Phycoerythrin (Ref. PJRS25) was purchased from ProZyme. Human Active MMP 1 and MMP 9 Fluorokine E kits were purchased from R&D Systems. MMP capture beads for MMPs 1, 2, 3, 7, 10 and 12 were purchased from R&D Systems (Human MMP Magnetic Luminex Performance Assays), and those for MMP 9 from Bio-Rad (Bio-Plex Pro Human MMP-9 Singleplex Set Ref. 171BM006M). Antibody-based bead capture was performed using reagents in the Human Magnetic Luminex Performance Assay Base Kit, MMP Panel (R&D Systems, Ref. LMPM000).

Methods

Synthesis of an Activity-Based Probe

A trifunctional, biotin-tagged hydroxamate benzophenone (HxBP-Bt) probe (containing a PEG linker) was aliquoted at 10 mM in DMSO and frozen at −80° C. Its structure is shown below:

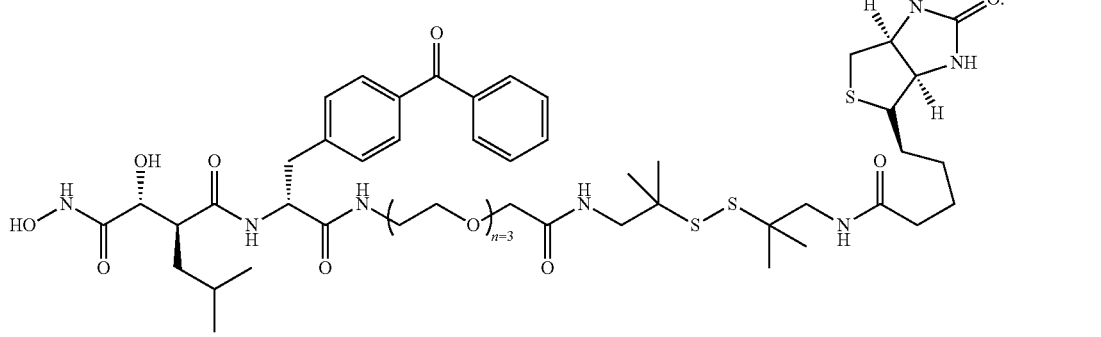

HxBP-Bt probe with PEG linker
Chemical structure of HxBP-Bt probe

Formula 1

Examples

The broad applications of the MAMBI technique were exemplified through characterizing MMP activity in samples related to the healthy regulation and dysregulation of endometrial tissue. Regulation of MMP activity within endometrial tissue mediates healthy menstruation (Osteen, et al., Validation of Active Site-Directed Labeling of MMP by HxBP-Bt The binding of an activity-based probe, e.g., HxBP-Bt, to the active site of an MMP (as shown in FIG. 1A) would effectively reduce (or inhibit) the ability of such MMP to cleave its substrate. The activity-based probe does not bind to zymogen or an inhibitor-bound MMP, as their active sites are occupied (as shown in FIG. 1B). Therefore, a correlation should exist between the activity-based probe-bound MMP, quantifiable via standard fluorescence measurement in multiplex bead array assays as shown in FIG. 1C, and the reduction (or "inhibition") in substrate cleavage by an active MMP. This correlation should also provide an $IC_{50}$ value to measure the sensitivity/potency of the MAMBI system to bind, and thereby quantify, active MMPs.

FRET-based studies were used to approximate average sample protease activities and the inhibitory properties of the PEG modified HxBP-Bt probe, following a protocol as previously described in (Miller et al., *Integrative Biology*, 3(4), 422-38 (2011)). Fluorescence resonance energy transfer (FRET) technique is used to determine if a substrate is cleaved by pre-labeling two parts of a substrate molecule with a donor chromophore and an acceptor chromophore, respectively, and measuring the energy transfer efficiency from the donor to the acceptor chromophore to determine if two fluorophores are within a certain distance of each other, i.e. the substrate is intact and uncleaved.

Here, HxBP-Bt bound MMP samples were mixed with chromophore-labeled substrate peptides in 384-well Opti-Plates® at 37° C. using timelapse fluorimetry in the Spectromax® M3 and M2e fluorimeters (Molecular Devices). The fluorescence was monitored by plate reader. In general, readings measured fluorescence every 20 minutes for roughly five hours and the reported rate of increase in fluorescence was calculated from fitting a linear portion of this increase including at least 4 data points and subtracting the average increase in background, protease-free conditions. All experiments were performed in technical triplicate and we excluded clear outliers in a few cases (<10% of all triplicates) using Dixon's Q-test with a 90% threshold. The excitation and emission wavelengths used were 485 nm and 530 nm, respectively. Reaction velocities were calculated from linear reaction periods from raw fluorescence value time courses.

Relative rates of FRET substrate cleavage among samples containing active proteases (without the addition of HxBP-Bt probe) were quantified and used as 100% MMP activity. Relative rates of FRET substrate cleavage among samples with the addition of HxBP-Bt were quantified and compared with the rates without HxBP-Bt.

Activities of recombinant MMPs 1, 7, 8, 12 and 13, in the presence or absence of HxBP-Bt probe, were characterized with PEPDAB008 (Dabcyl-Pro-Cha-Gly-Cys(Me)His-Ala-Lys(5-FAM)-NH2); MMPs 2 and 9 with PEPDAB011 (Dabcyl-Gly-Pro-Leu-Gly-Met-Arg-Gly-Lys(5-FAM)-NH2) and MMPs 3 and 10 with PEPDAB052 (Dabcyl-Ala-Pro-Phe-Glu-Met-Ser-Ala-Lys(5-FAM)-NH2). For all experiments, substrates were diluted from 5 mM stock in dimethyl sulfoxide (DMSO) to a final concentration of 10 µM in buffer of 50 mM Tris, pH 7.5, 150 mM NaCl, 2 mM $CaCl_2$, 5 mMZnSO$_4$, and 0.01% Brij-35.

The substrate concentration was normalized to a positive control, comprised of 10 mM substrate incubated with 0.5% trypsin and 0.2% EDTA (Sigma). FRET-based measurements of active enzyme concentrations supported the computation of approximated IC50 values, i.e., interpolated from a 6-point dilution curve of PA 12, which was incubated with 5 nM recombinant ADAM12, 10 min prior to mixing with the FRET-substrate solution. These IC50 values were used to estimate binding off-rates in the computational model. IC50 of the inhibitor was calculated by fitting the resulting dose-dependent data with the PRISM software (GraphPad, USA)

Validation of Specificity of MAMBI in Quantifying Active MMP

A single active recombinant MMP (5 nM by mass, 5 µL total vol) was incubated with HxBP-Bt (30 min at 37° C., 500 nM final HxBP-Bt concentration) under reversible binding conditions. Tested MMPs included MMP1, MMP2, MMP3, MMP7, MMP8, MMP9, MMP10, MMP12, and MMP13. Each containing biotin-labeled MMP (MMP reversibly bound to HxBP-Bt) was then incubated with a cocktail of MMP capture beads (60 minutes, RT, 25 µL total vol). These MMP capture beads were commercially available as described in the Materials section.

A cocktail of MMP capture beads diluted in Microparticle Diluent 3 (R&D systems; PN 895857) (17.5 µL bead suspension) was added to the HxBP-Bt-labeled sample (7.5 µL) in a 384-well plate (60 minutes, with rotary agitation, room temperature). Samples were washed 3 times with PBS 0.1% TWEEN®-20 (300 µl each wash) using the Magnetic BioTek plate washer (405 Select TS), incubated with Streptavidin-R-Phycoerythrin (10 µg/mL) diluted in diluted wash buffer concentrate (R&D systems; PN 895003) (15 minutes, with rotary agitation, room temperature), and again washed 3 times by plate washer. Samples were immediately characterized using the FLEXMAP 3D system (Luminex).

Results

1. Active Site-Directed Labeling on MMPs by HxBP-Bt Probe.

Figure 3:
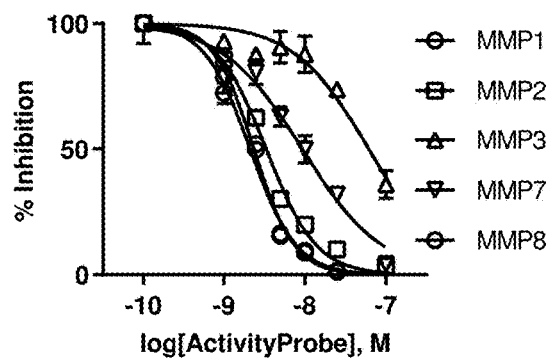
FIG. 3 is a line graph showing the inhibition (%) of MMP1, MMP2, MMP3, MMP7, and MMP8 over the amount of an activity-based probe, biotin-tagged hydroxamate benzophenone (HxBP-Bt), (mole; log scale).
Figure 4:
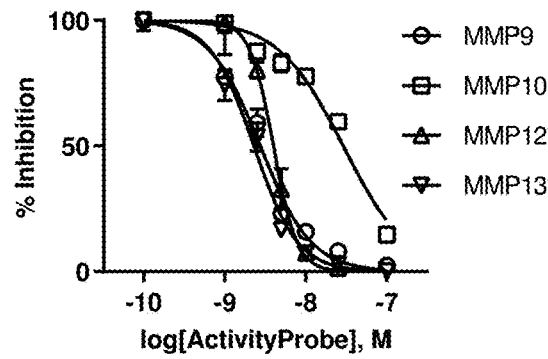
FIG. 4 is a line graph showing the inhibition (%) of MMP9, MMP10, MMP12, and MMP13 over the amount of HxBP-Bt probe (mole; log scale).

The binding of HxBP-Bt to the active site of an MMP (as shown in FIG. 1A) reduced (or inhibited) the ability of such MMP to cleave its substrate. This is unlike prototypical total-MMP quantification as shown in FIG. 1D, where the probe labels a non-active site of MMPs and does not distinguish between active MMP, zymogen, and tissue inhibitor-bound MMPs. FIGS. 3 and 4 show the correlation between the increase of the amount of active site-directed (i.e., activity-based) HxBP-Bt probes in an MMP solution and the reduction (or "inhibition") of the MMP to cleave a substrate.

Table 1 shows the $IC_{50}$ values of each tested MMP, calculated from FIGS. 3 and 4, as detected by the activity-based probe (HxBP-Bt) across different MMPs and the capture beads specific to each MMP for identification

TABLE 1

The inhibition of substrate cleavage ability of active MMPs as MMPs were bound by activity-based probe, HxBP-Bt.

| MMP | IC50 [nM]<br>(95% confidence) |
|---|---|
| 1 | 2.1 (1.9-2.3) |
| 2 | 3.3 (3.1-3.6) |
| 3 | 61 (49-80) |
| 7 | 9.2 (7.8-11.1) |
| 8 | 2.4 (2.1-2.6) |
| 9 | 2.7 (2.4-3) |
| 10 | 29 (24-35.3) |
| 12 | 4.0 (3.8-4.2) |
| 13 | 2.3 (2-2.5) |

2. Specificity of Capture Beads in Detecting Single MMPs in MAMBI.

Next, single active MMPs labeled with a biotin-tagged activity-based probe, e.g., HxBP-Bt, were individually incubated with a cocktail of MMP capture beads, each differently color-coded, capable of capturing MMP1, MMP2, MMP3, MMP7, MMP8, MMP9, MMP10, MMP12, and MMPP13. Following washes to remove un-captured MMP, further incubation of the labeled and captured MMP on the beads with streptavidin-R-Phycoerythrin allowed the latter to bind to biotin-tagged, activity-based labeled MMP, and therefore the activity-based labeled MMP be picked up by illumination of phycoerythrin.

Figure 5:
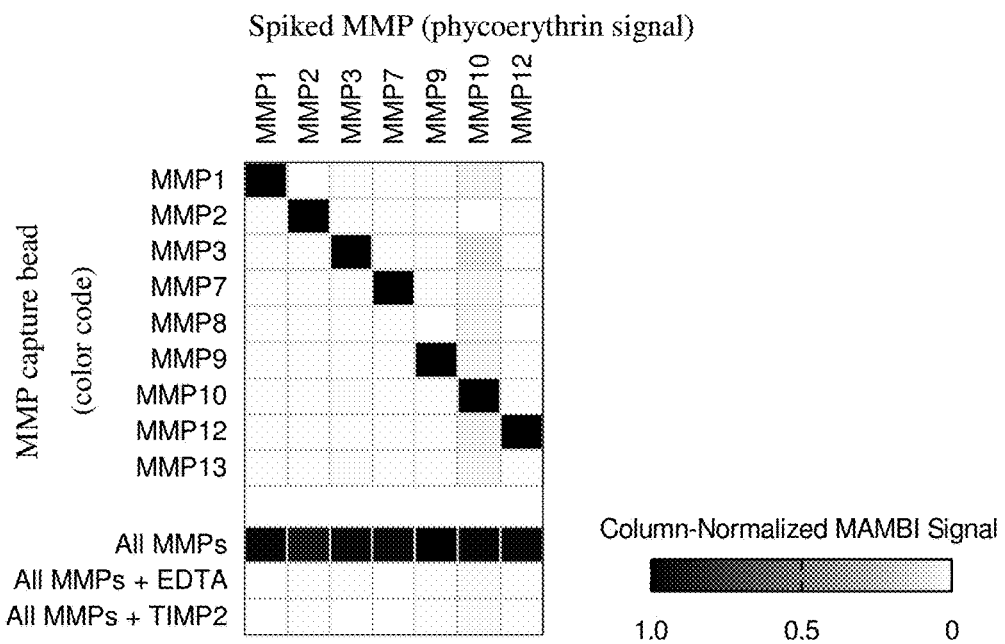
FIG. 5 is a chart showing the normalized signals of each single recombinant MMP in a solution containing a cocktail of beads, each labeled with a capture antibody specific for an MMP, showing the high selectivity in detecting single MMP with a cocktail of beads in the MAMBI.

Simultaneous detection of the color code and any phycoerythrin signal of each type of beads determined the specificity of the beads for capturing cognate MMP. FIG. 5 shows MMP1, 2, 3, 7, 9 and 12 capture beads had high specificity for detecting single recombinant MMPs in solution. Detection of MMP10 through the assayed capture beads was observed to have both a low absolute signal and a low relative specificity. This might be due to the low specificity and/or binding ability of the specific capture antibody in the assayed MMP10 capture bead from the commercial source. Therefore, MMP10 capture bead was removed from the MAMBI capture bead cocktail in subsequent studies.

Ethylenediaminetetraacetic acid (EDTA), a small molecule known to inhibit metalloprotease activity (as shown by the last model in FIG. 1B), completely eliminated HxBP-Bt binding (FIG. 5). This result validated the selectivity of the MAMBI system to quantify uninhibited, active proteases.

Figure 2:
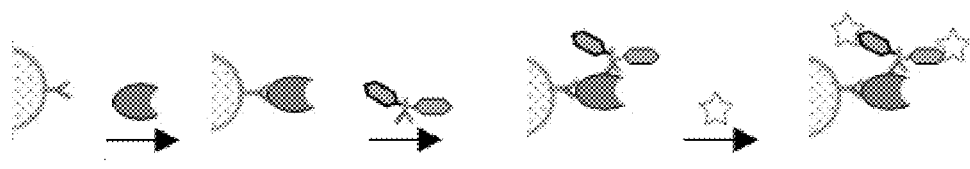
FIG. 2 is a schematic representation of a prototypical detection system where the total MMP is labeled including the three sub-types shown in FIG. 1B, because the tag-conjugated probe for MMP binds to the non-active site and therefore does not distinguish among active MMP, inhibited MMP, and zymogen.

In control experiments using a prototypical, total-MMP detection system (as shown by FIG. 2), EDTA did not eliminate the signal picked up by MMP capture bead, as the prototypical detection technique utilized probes that do not target the active sites of MMPs and therefore could not distinguish between active MMP and EDTA-bound MMP.

3. UV-Crosslinking Increased Stability of MMP Labeling by the Probe without Interfering with the MAMBI Signal in Detecting Single MMP.

Figure 6:
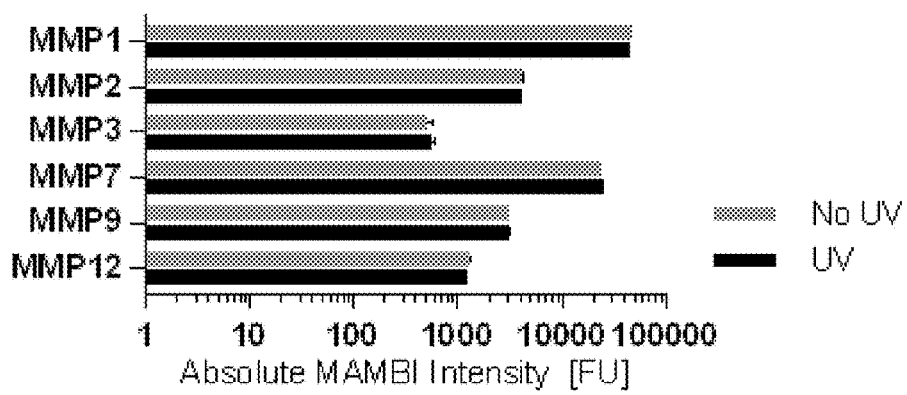
FIG. 6 is a bar graph showing the absolute fluorescence intensity in the detection of different MMPs using the MAMBI system, where the activity-based probe, HxBP-Bt, after binding to target MMP has been or has not been UV crosslinked, showing the detection is minimally sensitive to UV crosslinking between the probe and a target MMP.

UV-mediated crosslinking (5 minutes 150 mwatts/cm$^2$; PK50 Omnicure series 2000 lamp with a 365 nm filter) of the benzophenone group of HxBP-Bt to the MMP active sites did not alter or increase the observed absolute intensity of MAMBI-labeled beads. FIG. 6 shows detection of single MMPs in the MAMBI system had minimal sensitivity to UV crosslinking. Tests confirmed UV-mediated crosslinking was necessary for the covalent labeling of recombinant MMP-9, which was consistent with previous studies in (Saghatelian, et al., *Proceedings of the National Academy of Sciences of the U.S.A.*, 101(27):10000-5 (2004); Sieber, et al., *Nature Chemical Biology*, 2(5), 274-81 (2006)). Together, these results suggest that the tight bonding of HxBP-Bt to active MMPs, combined with the gentle process conditions in MAMBI detection (e.g., mild buffers, room temperature, <4 hours) allowed for significant utilities of the MAMBI system in detecting active MMPs without introducing process variability commonly associated with UV crosslinking (Klein et al., *ChemMedChem*, 4(2), 164-70 (2009); Dormin, et al., *Chemical Reviews*, 116(24):15284-15398 (2016)). UV crosslinking did not interfere with MAMBI detection and thus can readily be incorporated into the sample processing workflow to improve the stability HxBP-Bt labeling.

Example 2. Superior Sensitivity and Linear Range of MAMBI Detection of Active MMPs Dilutions of active recombinant proteases to known concentrations and testing them in the MAMBI system determined the sensitivities and linear ranges of MAMBI detection. All dilutions were performed with a background of 1% BSA.

Table 2 shows the capture beads targeting MMPs 1 and 7 in a MAMBI system had a wide detection range, and all assayed capture beads demonstrated consistently low background fluorescent intensities.

TABLE 2

The range of linear relationship between the detection signal in the exemplified MAMBI system and the concentration of active MMPs.

| MMP | Recombinant MMP MAMBI Linear Range of Detection | |
|---|---|---|
| | Min FU | Max FU |
| 1 | 80 | 40,000 |
| 2 | 80 | 430 |
| 3 | 60 | 260 |
| 7 | 65 | 18,000 |
| 9 | 70 | 820 |
| 12 | 150 | 284 |

The absolute sensitivity of MAMBI detection for each target MMP was approximated based on the absolute concentration of the standard diluent at the limit of detection (LoD). The molar concentrations of active MMP in diluted standards were estimated in three ways as shown in Table 3. The upper limit of active protease concentration assumed 100% activity of the reconstituted commercially produced protein, where the active concentration corresponded to the mass of total protein in the sample. However, recombinant solutions of activated MMPs were known to have incomplete activity in solution (Nury, et al., *Chembiochem*, 14(1): 107-14 (2013); Nakai, et al., *Bioorganic & Medicinal Chemistry*, 17(3), 1101-8 (2009)). Concentrations of the subpopulation of active MMPs were directly measured both by monitoring the FRET cleavage of substrates with known catalytic efficiencies (Miller M, et al., *Integrative Biology*, 3(4), 422-38 (2011))) and with the commercially available Human Active MMP Fluorokine E Kits (R&D Systems).

TABLE 3

Absolute limits of detection of active MMPs by the MAMBI system estimated by measurements following three approaches.

| | Estimated MAMBI Limit of Detection | | |
|---|---|---|---|
| MMP | by mass [M] | by FRET activity [M] | by kit Fluorokine E [M] |
| 1 | 7E−15 | 2E−17 | 1E−18 |
| 2 | 6E−11 | 6E−14 | — |
| 3 | 3E−11 | 1E−13 | — |
| 7 | 2E−13 | 4E−15 | — |
| 9 | 4E−12 | 9E−15 | 8E−16 |
| 12 | 6E−11 | 4E−13 | — |

The MAMBI detection limit of active MMP 9, gelatinase, was 800 attomole ($800 \times 10^{-18}$ M=$8 \times 10^{-16}$ M) as approximated by Fluorokine E activity measurements (Table 3). This detection limit approaches the previously reported detection limit of 100 attomole active MMP 9 by zymography (Bregant et al., *Journal of Proteome Research*, 8(5): 2484-2494 (2009)), but zymography fails to resolve the fully active form from TIMP-inhibited forms. MAMBI detection further allowed for sensitive activity measurements of matrilysin (MMP-7) and collagenases (MMPs 1 and 8), which are difficult to detect using zymography. Standard curve fitting indicated that MAMBI was able to detect active MMP-1 at concentrations less than 100 molecules per μL sample.

Notably, these detection limits dramatically surpassed the ~3 nM limit of detection demonstrated by conventional activity-based protein profiling approaches shown in (Saghatelian, et al., *Proceedings of the National Academy of Sciences of the U.S.A.*, 101(27):10000-5 (2004); Chan, et al., *Journal of the American Chemical Society*, 126(44), 14435-46 (2004); Nury, et al., *Chembiochem*, 14(1):107-14 (2013)).

Example 3. Identification and Quantification of Active MMPs in Conditioned Media (Supernatants from Cell Cultures) Responsible for Proteolytic Activity Materials & Methods Eight conditioned mediums were assayed, each tested in two complete biological replicates (n=2), from these cell cultures: four endometrial related cell populations including (1) primary endometrial stromal cells (pESC), (2) telomerase-immortalized human endometrial stromal cells (tHESC) (Krikun et al., *Endocrinology*, 145(5):2291-6 (2004)), (3) an adenocarcinoma endometrial epithelial cell line, Ishikawa, and (4) an epithelial line derived from an endometriosis lesion, 12z; three canonical cancer cell lines including (5) A549, (6) MD-MBA-321, and (7) HT1080; as well as (8) human telomerase reverse transcriptase (hTERT) immortalized mesenchymal stem cell line (MSC).

Conditioned supernatant was prepared: collected at 12 h, spun down at 200 g for 5 min to remove debris, and immediately flash-frozen. For FRET-substrate assays involving this supernatant, final reactions were composed of a 2:1:1 mixture of 20 mM substrate diluted from 5 mMDMSO stock into phosphate buffered saline, 4 nM active MMP7 diluted in 'MMP buffer', and thawed supernatant.

| Conditioned cell medium | |
|---|---|
| t = 0 | Seed - 770,000 cells/10 cm plate in FSM |
| t = 12 hrs | Wash PBS culture 36 hours 7 ml SFM |
| t = 48 hrs | Count cells; concentrate medium 20x with 3k cut off filter |
| t = 50 hrs | Freeze conditioned media and do BCA |

The 12Z cell line was generously provided by Anna Starzinski-Powitz (University of Frankfurt) by way of Steve Palmer (EMD Serono). Cell line authenticity was determined by short tandem repeat (STR) profiling (GRCF DNA services; Johns Hopkins University) following the ANSI/ATCC ASN-0002-2011 Authentication of Human Cell Lines standardized procedure. An 80% match threshold from 8 STR loci was not met with any other cell type using either the ATCC (Masters algorithm) or ANSI (ANSI algorithm) methods when compared against cell line databases, of which 12Z was not a member.

Previous matrix metalloproteinase (MMP) profiling 13 of MMP-1, -2, -3, -7, and -9 matched levels reported elsewhere for 12Z, as did profiling of TIMPs and EGFR62. 12Z were routinely cultured in media that consisted of DMEM/F12 supplemented with 100 U/ml penicillin, 100 µg/ml streptomycin (Invitrogen), along with 10% fetal bovine serum (Atlanta Biologicals; Atlanta, Ga.) at 37° C., 5% $CO_2$. Cancer cell lines were obtained from ATCC and Asterand (SUM149PT) and were cultured according to manufacturer's guidelines. siRNA The MDA-MB-231 cell line (ATCC) was cultured according to manufacturer's guidelines in DMEM supplemented with 10% FBS and penicillin-streptomycin. The cells were grown at 37° C. in a humidified incubator maintained at 5% $CO_2$. Once 80-90% confluent, the cells were changed to serum-free medium for 24 hours prior to the collection of the supernatant. The serum-free supernatant which contained proteases secreted by the breast cancer cells were then used for a protease assay.

Validation of HxBP-Bt probe binding to the active sites of proteases in conditioned media was performed based on the FRET-based study as described in Example 1, without the addition of MMP capture beads.

Identification of specific active MMPs in these media was performed in a MAMBI system (with the use of MMP capture beads as shown in FIG. 1C). Immediately prior to a MAMBI assay, samples containing active proteases were thawed on ice and diluted to the target concentration in MMP-buffer (10 µM in buffer of 50 mM Tris, pH 7.5, 150 mM NaCl, 2 mM $CaCl_2$, 5 mM $ZnSO_4$, and 0.01% Brij-35). Samples solutions (≥5 µL) were mixed with HxBP-Bt (½ sample volume of 1500 nM HxBP-Bt solution in MMP-buffer-final 500 nM HxBP-Bt), covered to limit evaporation and incubated for 30 min at 37° C. A cocktail of MMP capture beads diluted in Microparticle Diluent 3 (R&D systems; PN 895857) (17.5 µL bead suspension) was added to the HxBP-Bt-labeled sample (7.5 µL) in a 384-well plate (60 minutes, with rotary agitation, room temperature). Samples were washed 3 times with PBS 0.1% Tween-20 (300 µl each wash) using the Magnetic BioTek plate washer (405 Select TS), incubated with Streptavidin-R-Phycoerythrin (10 ug/mL) diluted in diluted wash buffer concentrate (R&D systems; PN 895003) (15 minutes, with rotary agitation, room temperature), and again washed 3 times by plate washer. Samples were immediately characterized using the FLEXMAP 3D system (Luminex).

Results

1. Validation of HxBP-Bt Probe Labeling/Binding to the Active Sites of Proteases and Consequently Inhibiting their Metalloprotease Activity.

Aggregate metalloprotease activity was approximated by monitoring FRET substrate cleavage of conditioned medium normalized to 1000 µg/mL, using a substrate that had previously been characterized as having high susceptibility to cleavage by a wide range of MMPs (Miller M, et al., *Integrative Biology*, 3(4), 422-38 (2011)).

Figure 7:
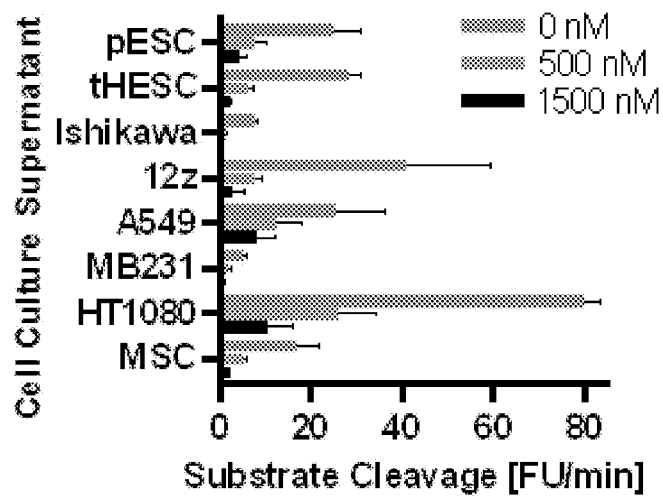
FIG. 7 is a bar graph showing the rate of cleavage of substrates (e.g., peptide), characterized by change in fluorescence per minute, in different conditioned media for different cell lines, in the absence (0 nM) or presence (500 nM, or 1500 nM) of the activity-based probe, HxBP-Bt. (n=2 biological replicates, mean±standard deviation, SD).

Cleavage profiles were generally consistent across the two biological replicates of each conditioned medium and represented the aggregate activity of multiple proteases in each medium. FIG. 7 shows FRET cleavage without HxBP-Bt probe (0 nM) showed a range of bulk protease activities in each of the eight conditioned media; adding 500 nM HxBP-Bt greatly deceased the substrate cleavage ability; and in some cases 1500 nM HxBP-Bt further decreased the protease activities. This validated the activity-based labeling of MMPs via binding of the HxBP-Bt probe to the active site of MMPs, which effectively reduced the substrate cleavage ability of such MMPs.

2. Identification of MMPs Responsible for Proteolytic Activity in the Conditioned Media Via MAMBI Assays.

Figure 8A:
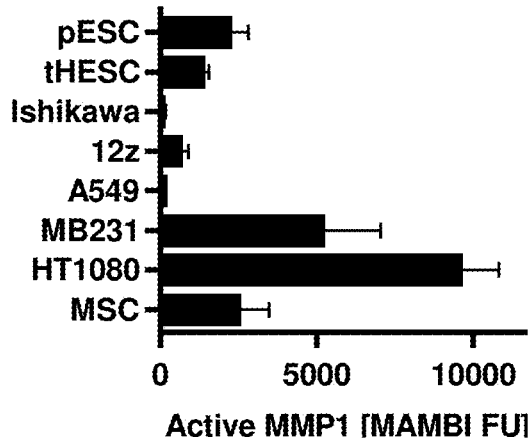
FIG. 8A is a bar graph showing the relative amount of active MMP1 in different conditioned media (normalized to 1000 µg/mL) corresponding to those shown in FIG. 7, as detected by the MAMBI system in a fluorescent unit, n=2 biological replicates, mean±SD.
Figure 8B:
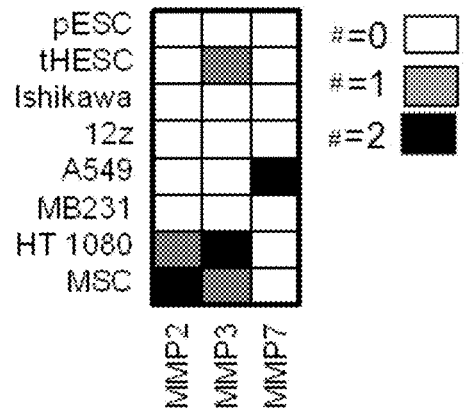
FIG. 8B is a chart showing, for each of the conditioned media, the number of biological replicates that are detected positive (above the limit of detection in the MAMBI system) for MMP2, MMP3, or MMP7.

MAMBI assays of each of the eight conditioned media revealed the identities of a subset of proteases responsible for the proteolytic activities seen in these media. FIG. 8A shows that MAMBI assays detected MMP1 in all conditioned media, i.e., MMP1 was above the limit of detection (LoD) afforded by the MMP1 capture bead of the MAMBI system in both of the two biological replicates of all conditioned media. MMP2 was above the LoD afforded by the MMP2 capture bead of the MAMBI system in both (#=2) of the two biological replicates of MSC supernatant/conditioned medium, as well as in one biological replicate (#=1)

out of the two of HT1080 conditioned medium, but not detectable in other conditioned media (#=0) (FIG. 8B). MMP3 was above the LoD afforded by the MMP3 capture bead of the MAMBI system in both (#=2) of the two biological replicates of HT1080 supernatant/conditioned medium, as well as in one biological replicate (#=1) out of MSC conditioned medium and of tHESC medium, but not detectable in other conditioned media (#=0) (FIG. 8B). MMP7 was above the LoD afforded by the MMP7 capture bead of the MAMBI system in both (#=2) of the two biological replicates of A549 supernatant/conditioned medium (FIG. 8B), which showed its active form, active MMP7, along with MMP1, contributed to the proteolytic activity of A549 conditioned medium. MAMBI assays did not detect MMP 9 or MMP 12 in any of the supernatants from the eight cell lines.

Notably, the commercial MMP1 activity detection kit (Fluorkine E, R&D Systems) was unable to detect active MMP1 above background in any of the eight conditioned media even within a 20 µl sample volume compared with 5 µl for MAMBI assays.

Example 4. Identification and Quantification of Active MMPs Responsible For Proteolytic Activity in Peritoneal Fluids from Control Donors and Patients Endometriosis Materials & Methods Clarified peritoneal fluid from patients with endometriosis was compared to that from a control population with regards to the active MMP compositions and quantities. Peritoneal fluid is a mixture of cell debris, leukocytes, and thousands of soluble proteins including over 100 proteases and protease inhibitors that is contained within the pelvic cavity and interacts with endometriotic lesions (Amon, et al, *PLoS ONE*, 5(6) (2010)).

Clinical Subjects and Procedures

All laparoscopy patients provided informed consent in accordance with a protocol approved by the Partners Human Research Committee and the Massachusetts Institute of Technology Committee on the Use of Humans as Experimental Subjects. Enrollment was limited to pre-menopausal women with regular cycles (26-32 days) and excluded individuals who had received hormonal treatment within three months of surgery. Moderate/Severe (Stage III/IV) endometriosis was diagnosed according to the revised criteria of the American Society for Reproductive Medicine 8. Peritoneal fluid was aspirated from the rectouterine pouch immediately following trocar insertion and prior to peritoneal lavage or surgical manipulation. Upon collection, specimens were immediately placed on wet ice and clarified within 15 min. by centrifugation for 10 min. at 1000 rcf. Clarified aspirates were transported to the laboratory on ice, aliquoted, and stored at −80° C. until analysis.

Results

Figure 9:
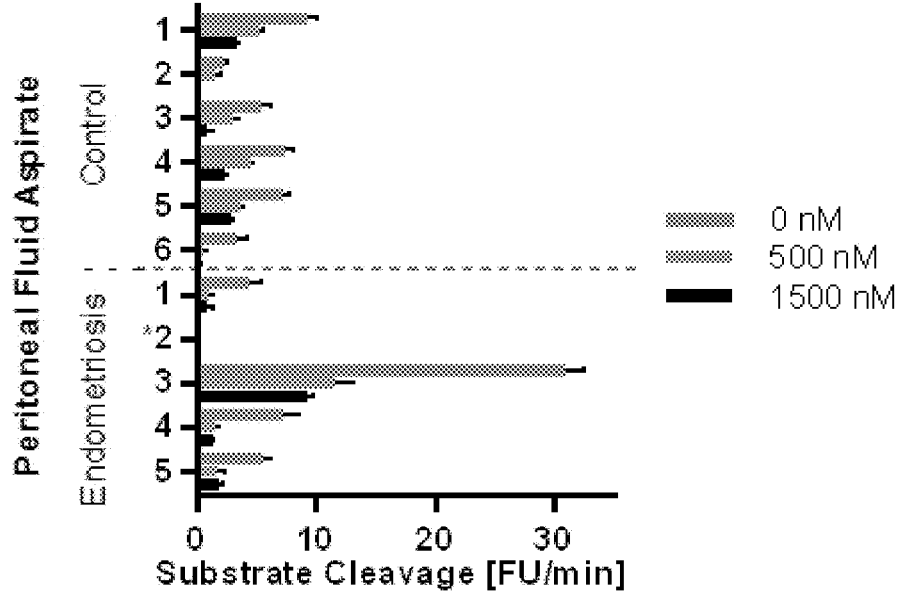
FIG. 9 is a bar graph showing the rate of cleavage of substrates (e.g., peptide), characterized by change in fluorescence per minute, in clarified peritoneal fluids from six control donors and from six endometriosis patients, assayed in the absence (0 nM) or presence (500 nM, or 1500 nM) of HxBP-Bt.

FIG. 9 shows HxBP-Bt inhibited substrate cleavage in all samples with varied efficiencies, which validated that the HxBP-Bt probe labels MMPs at their active sites.

Figures 10A, 10B:
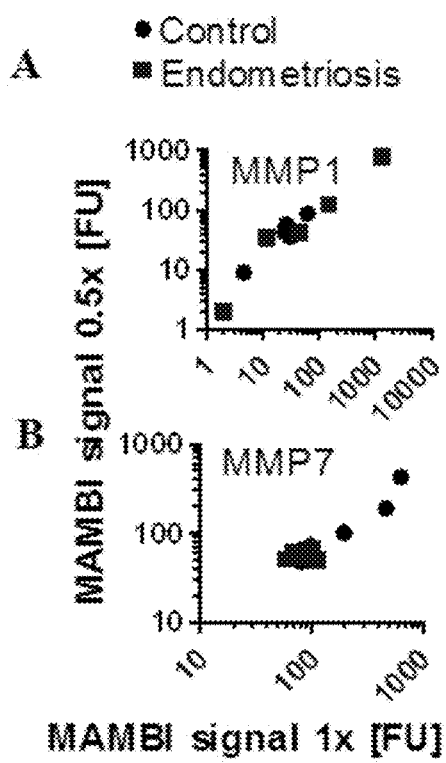
FIGS. 10A and 10B are dot graphs showing the absolute signal (fluorescence) of MMP1 (FIG. 10A) and MMP7 (FIG. 10B), respectively, from the MAMBI assay of diluted aspirate samples of peritoneal fluids from six control donors (denoted by the round symbol) and from endometriosis patients (denoted by the square symbol).
Figures 11A, 11B:
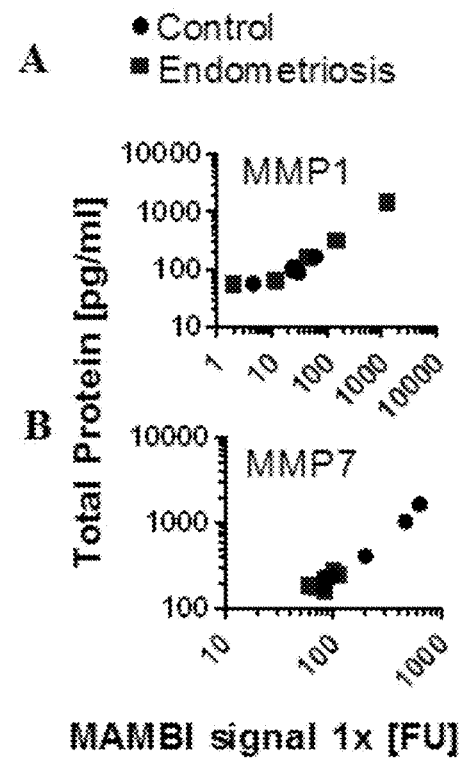
FIGS. 11A and 11B are dot graphs showing the total protein levels (pg/mL) compared to the absolute signal (fluorescence) of MMP1 (FIG. 11A) and MMP7 (FIG. 11B), respectively, from the MAMBI assay of peritoneal fluids from six control donors (denoted by the round symbol) and from endometriosis patients (denoted by the square symbol).

FIGS. 10A and 10B show MMP1 and MMP7 were detected by MAMBI assays in all samples with strong correlations between values detected in a diluted sample. FIGS. 10C and 10D show MMP1 and MMP7 were detected by MAMBI assays in all samples with strong correlations with the total protein values.

Although increased MMP2 activity was previously identified as associated with the diseased state (Chen et al., *Journal of American Chemical Society*, 135i, 1645-1648 (2013)), MAMBI assays here showed active MMP2 activity as well as active MMP 3, 9 and 12 were below the limit of assay detection. Notably, sample E2 had erythrocyte contamination which prohibited optical FRET activity measurements, but still allowed MAMBI processing.

Taken together, the levels of MAMBI detected active protease in Examples 3 and 4 highlighted the differences of MAMBI-based detection and other conventional detection strategies. Although active MMPs may be observed in two-dimensional cell culture by zymography, true functionally active concentrations of specific enzymes, such as those identifiable in MAMBI assays, are not revealed by zymography, because zymographic processing fails to preserve in situ native protein inhibition. Comparison of protease activity between control and diseased samples as shown in Example 4 demonstrates the applications of MAMBI as a companion diagnostic test. The panel of detectable active proteases is readily expandable and can be coupled with in situ labeling for more clinical applications of the MAMBI system.

Example 5. High Throughput Characterization of MMP Inhibitors in Complex Samples Background Conventional substrate cleavage assays are used to screen metalloprotease inhibitors by monitoring the decrease in FRET cleavage over a titration of the lead compound (Lauer-Fields et al., *Bioorganic and Medicinal Chemistry*, 17(3):990-1005 (2009); Hai et al., *Analytical Chemistry*, 83(1):425-430 (2011)). To date rapid screens for metalloprotease inhibitors based on competitive-ABPP techniques have been demonstrated only in well-defined single enzyme samples monitored by fluorescence polarization (Antczak et al., *Journal of Biomolecular Screening*, 13(4):285-94 (2008)) or lower throughput formats that rely on mass spectrometry (MS)-based (Saghatelian et al., *PNAS*, 101 (27):10000-5, (2004); Sieber et al., *Nature Chemical Biology*, 2(5):274-81 (2006)) or gel-based (Nakai et al., *Bioorganic & Medicinal Chemistry*, 17(3): 1101-8 (2009); Chan et al., *JACS*, 126(44):14435-46 (2004)) analysis.

Materials

Ten commercially available inhibitors were used. Their sources are shown in Table 4, and their chemical structures shown in formulae 2-11 corresponding to inhibitors 1-10.

TABLE 4

Commercially available metalloprotease inhibitors used in the assay.

| Common Name | Vendor | Part Number | Stock Soln in DMSO (mM) |
| --- | --- | --- | --- |
| Marimastat | Calbiochem | 444289 | 150 |
| Batimastat | Calbiochem | 196440 | 10 |
| Ro 32-3555 (Trocade) | Tocris | 2916 | 100 |
| MMP3 Inhibitor VII | Calbiochem | 444280 | 5 |
| ARP 101 | Tocris | 2622 | 50 |
| ARP 100 | Tocris | 2621 | 100 |
| UK 370106 | Tocris | 2900 | 100 |
| PF 356231 | Enzo | BML-PI155 | 5 |
| SB-3CT | Enzo | BML-EI325 | 5 |
| MMP Inhibitor 2 IV | Calbiochem | 444294 | 20 |

TABLE 4-continued

Commercially available metalloprotease inhibitors used in the assay.

| Common Name | Vendor | Part Number | Stock Soln in DMSO (mM) |
|---|---|---|---|

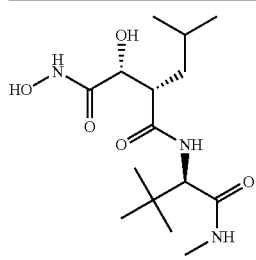

Formula 2. Marimastat

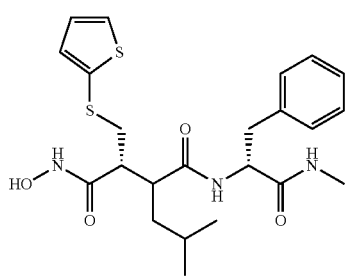

Formula 3. Batimastat

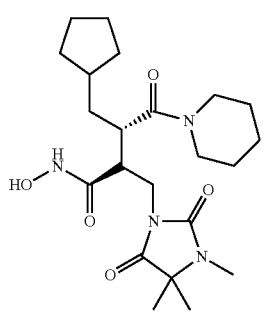

Formula 4. Ro 32-3555

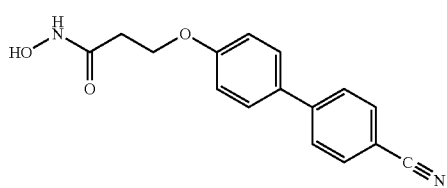

Formula 5. MMP-3 Inhibitor VII

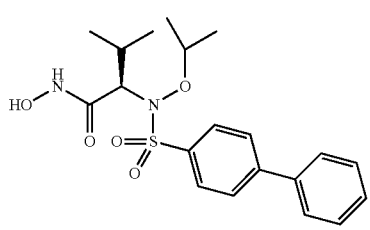

Formula 6. ARP 101

TABLE 4-continued

Commercially available metalloprotease inhibitors used in the assay.

| Common Name | Vendor | Part Number | Stock Soln in DMSO (mM) |
|---|---|---|---|

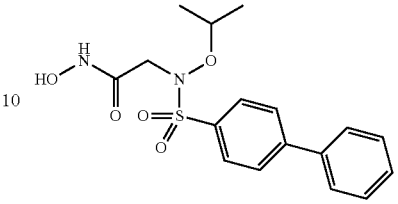

Formula 7. ARP 100

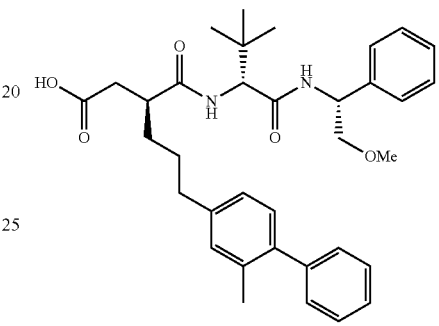

Formula 8. UH 370106

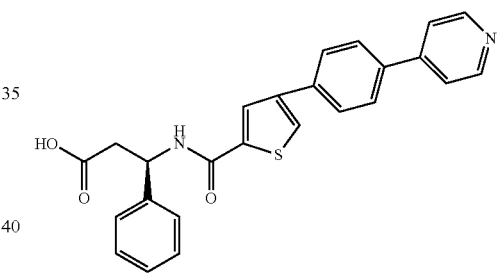

Formula 9. PF 356231

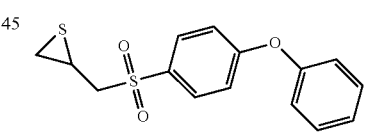

Formula 10. SB-3CT

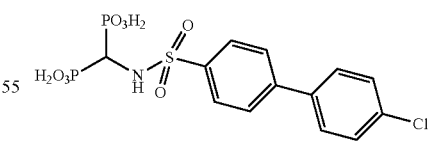

Formula 11. MMP-2 Inhibitor IV

Methods

The MAMBI platform was utilized for characterization of inhibitors, in which the HxBP-Bt probe binding to active metalloproteinase was assayed in the presence of small molecule metalloproteases inhibitors. The relative inhibitor potencies were quantified by the loss of labeling by activity-based probe of a target protease with the addition of a competitive inhibitor. Selectivity was additionally estimated by monitoring relative potencies across an enzyme super-family.

Figure 12A:
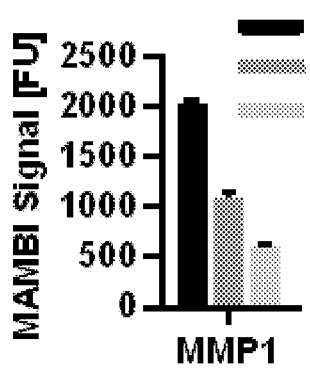
FIGS. 12A and 12B are bar graphs showing the approximate linear MAMBI signal (fluorescence) over series diluted clarified menstrual effluent (at 4%, 2%, and 1%) for MMP1 (FIG. 12A) and for MMP2, MMP3, and MMP7 (FIG. 12B).
Figure 12B:
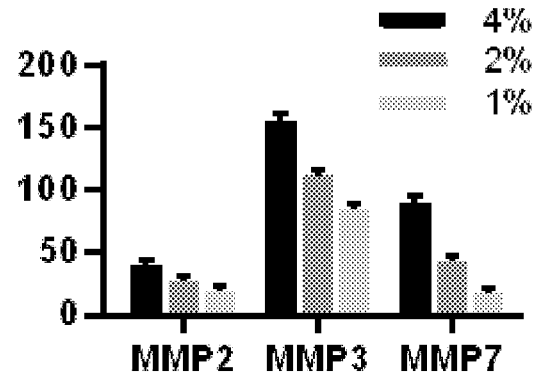

The relative inhibition by 10 commercially available inhibitors was characterized in a mixture of six recombinant MMPs, as well as in menstrual serum effluent. For the menstrual serum effluent, MAMBI measurements of diluted menstrual effluent identified native active MMP1, 2, 3 and 7 as having sufficient sensitivity, suitable for use in characterizing competitive inhibitor potencies (FIGS. 12A, 12B).

Each competitive inhibitor was titrated to be 0.33×, 1×, 3× or 15× (times) the concentration compared to that of the HxBP-Bt probe (the probe was constant at 0.5 µM; each inhibitor was tested in 0.17 µM, 0.5 µM, 1.5 µM, and 7.5 µM, respectively), and incubated with sample and the HxBP-Bt probe. Protease labeling was reported as a fraction of MAMBI signal without competitive inhibition.

Results

Figure 13:
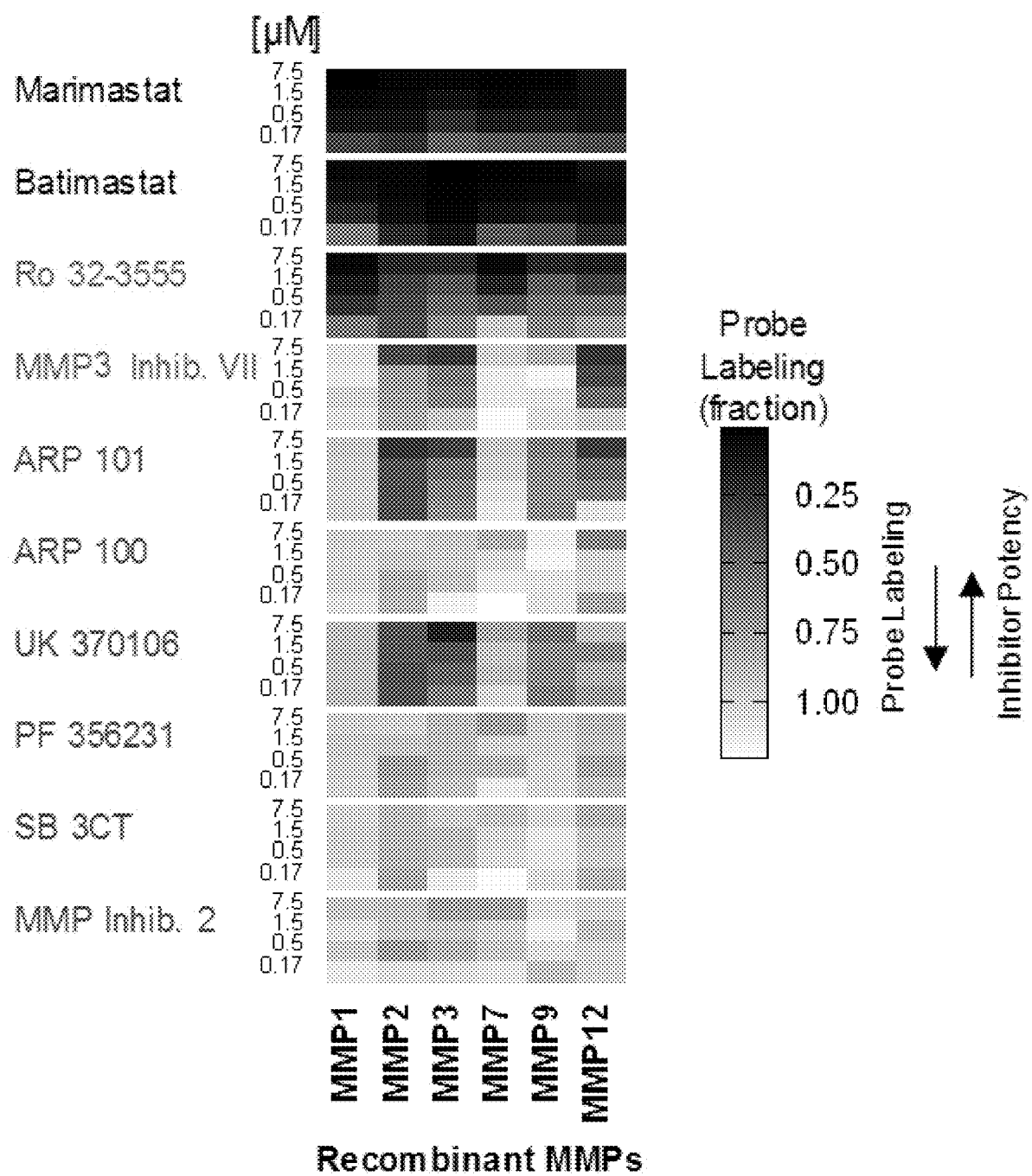
FIG. 13 is a chart showing the fraction of each of the six recombinant MMPs (including MMP1, MMP2, MMP3, MMP7, MMP9, and MMP12) being labeled by the HxBP-Bt probe in the presence of different competitive inhibitors (including Marimastat, Batimastat, Ro32-3555, MMP3 Inhibitor VII, ARP 101, ARP 100, UK 370106, PF 356231, SB 3CT, and MMP2 inhibitor).

FIG. 13 shows the fraction of each of the six recombinant MMPs being labeled by the probe in the presence of ten inhibitors, which indicates the selectivity of metalloprotease inhibitors against a panel of MMPs. The smaller the probe labeling fraction, the greater the inhibition potency.

Figure 14:
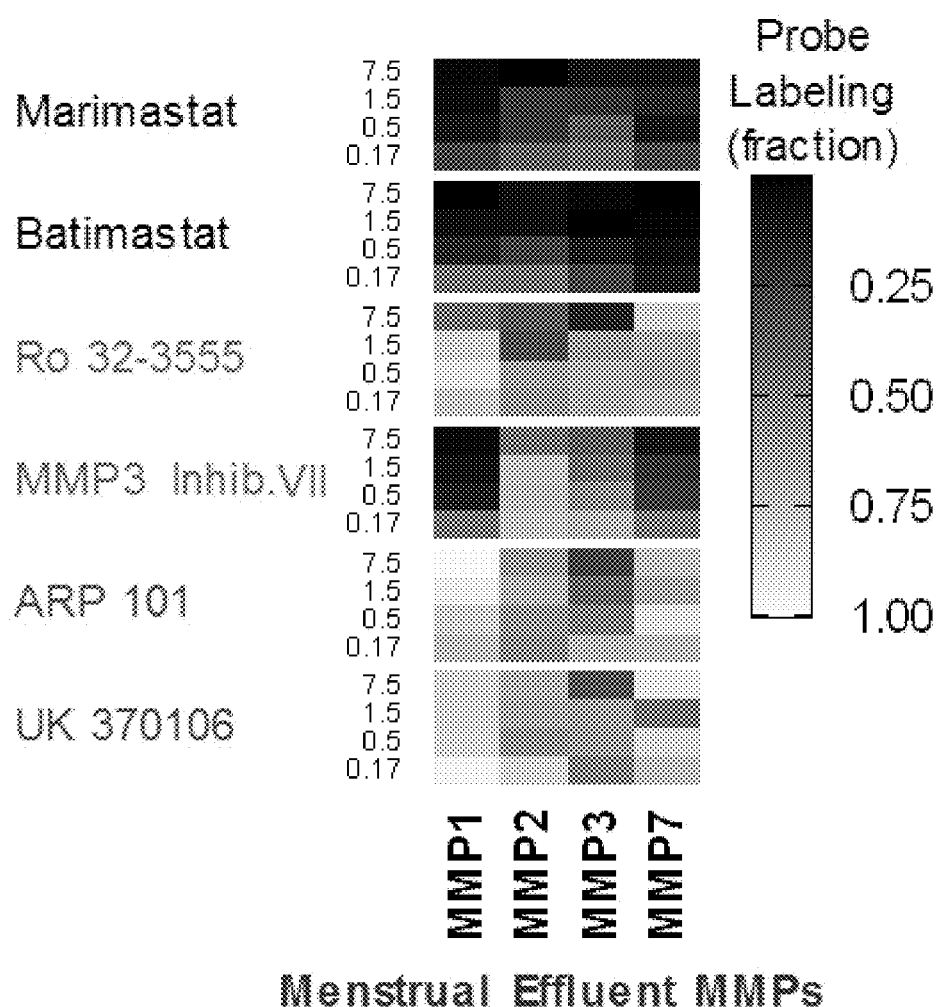
FIG. 14 is a chart showing the fraction of each of the four MMPs from menstrual effluents (including MMP1, MMP2, MMP3, and MMP7) being labeled by the HxBP-Bt probe in the presence of different competitive inhibitors including Marimastat, Batimastat, Ro32-3555, MMP3 Inhibitor VII, ARP 101, and UK 370106.

FIG. 14 shows the fraction of each of the four MMPs from menstrual serum effluent being labeled by the probe in the presence of six inhibitors, which indicates the selectivity of metalloprotease inhibitors against a panel of MMPs. The smaller the probe labeling fraction, the greater the inhibition potency.

Taken together, inhibition profiles in both recombinant MMPs and menstrual effluent as characterized by competitive-MAMBI (shown in FIGS. 13 and 14) closely followed the relative inhibition potencies established in literature.

Marimastat and Batimastat showed expected profiles as promiscuous inhibitors with inhibitory activity toward every protease tested. Notably when assessed in both recombinant and effluent derived samples, Batimastat showed stronger inhibitory activity against MMP3 compared with Marimastat, where Batimastat is indeed known to have increased potency toward MMP-3 (IC50 20 nM) compared with Marimastat (IC50 200 nM) (Vandenbroucke & Libert, Nature Reviews Drug Discovery, 13(12):904-917 (2014)). ARP 101 demonstrated increased potency towards MMP2 and MMP3 compared to the closely related but less lipophilic ARP 100, which was consistent with its described range of activity (Nuti et al., Journal of Medicinal Chemistry, 52(15):4757-4773 (2009)). Ro 32-3555 showed expected significant potency towards MMP1 and MMP7 (Close, Annals of the Rheumatic Diseases, 60 Suppl 3, iii62-7 (2001)) in both recombinant and effluent derived samples, whereas MMP Inhibitor 3 VII and UK 370106 exhibited expected inhibition of MMP3. The gelatinase inhibitors, SB-3CT and MMP Inhibitor 2 did not prevent the binding of HxBP-Bt to those enzymes which was attributable to their low overall potency compared with HxBP-Bt and their mechanism-based inhibition.

The strong overall concordance with known inhibition validated the MAMBI platform for characterization of metalloprotease inhibitor potencies; and further exemplified the high throughput screening capability, the selectivity characterizations, and the quantification of relative levels of active proteases (especially in the presence of competitive inhibitors), supported by the MAMBI platform, which was not realized by existing techniques.

Table 5 summarizes the established inhibition potencies of these inhibitors in literature: Marimastat (Vandenbroucke & Libert, 2014); Batimastat (Vandenbroucke & Libert, 2014); Ro 32-3555 (Close, 2001); MMP inhibitor 3 VII (CalBioChem Catalog); ARP 101 (Nuti et al., 2009); ARP 100 (Nuti et al., 2009); UK 370106 (Fray, Dickinson, Huggins, & Occleston, 2003)(MMP 7 from SCBT website); PF 356231 (Morales et al., 2004); SB 3CT (Vandenbroucke & Libert, 2014); MMP inhibitor 2 (Rubino et al., 2011).

TABLE 5

Summarized inhibition potencies of inhibitors as singly or individually reported in the literature.

| | Probe 1 IC50 nM | Marimastat IC50 nM | Batimastat IC50 nM | Ro32-3555 Ki nM | MMP Inhib 3 VII IC50 nM | ARP 101 IC50 nM | ARP 100 IC50 nM | UK 370106 IC50 nM | PF 356231 IC50 nM | SB 3CT Ki nM | MMP inhibitor 2 IC50 nM |
|---|---|---|---|---|---|---|---|---|---|---|---|
| MMP1 | 2 | 5 | 3 | 3 | | 490 | 12000 | 20% 100 uM | | 206000 | |
| MMP2 | 3 | 6 | 4 | 154 | | 0.8 | 12 | 34200 | >100 | 14 | 37 |
| MMP3 | 61 | 200 | 20 | 527 | 25 | 50 | 5900 | 23 | 0.39 | 15000 | |
| MMP7 | 9 | 20 | 6 | 42 | | | | 5800 | 96000 | | |
| MMP9 | 3 | 3 | 1 | 95 | | 6.7 | 200 | 30400 | 0.98 | 600 | >1000 |
| MMP12 | 2 | | | | | | | 42 | 1.4 | | |

Compared to these existing methods, competitive-MAMBI offers improved throughput and multiplexing, minimal sample requirements, and ready adoption to more complex and physiologically relevant protease samples. These inhibitor studies also supported the high throughput characterization of novel metalloprotease inhibitors by the competitive-MAMBI platform.

In summary, the examples demonstrated a platform for multiplexed active metalloprotease detection in complex samples by integrating components of activity-based protein profiling and bead-based immunoassays. The MAMBI technology detected relative levels of active recombinant MMPs 1, 2, 3, 7, 9, and 12 and those same MMPs in cell culture supernatant, peritoneal fluid aspirates, and menstrual fluid effluent, using small sample volumes. Here, the relative concentrations were reported, and the MAMBI detection is also applicable for absolute quantifications, e.g., via comparison to calibration curves of known concentrations of active proteases. The MAMBI platform is also readily applicable for detecting and characterizing other metalloproteases. Competitive-MAMBI is introduced in Example 5 as a complementary platform to evaluate the relative potency and selectivity of a panel of inhibitors across a range of MMPs in complex medium. The ability to assay multiplexed MMP activity in complex biological samples represents a significant improvement over established techniques for high throughput screening of metalloprotease inhibitors.

Example 6. Other Activity-Based Probes for Labeling Active MMPs

In Examples 1-5, HxBP-Bt probe was used in assays due to its tight binding to the targeted MMPs. Lower affinity probes are useful for screening the selectivity of competitive protease inhibitors as small molecule therapeutics. A wide range of other activity-based probes were also readily integrated to expand detection capabilities of the MAMBI platform to other proteases.

An alternative activity-based probe is denoted as ActivityProbeB, whose structure is shown below:

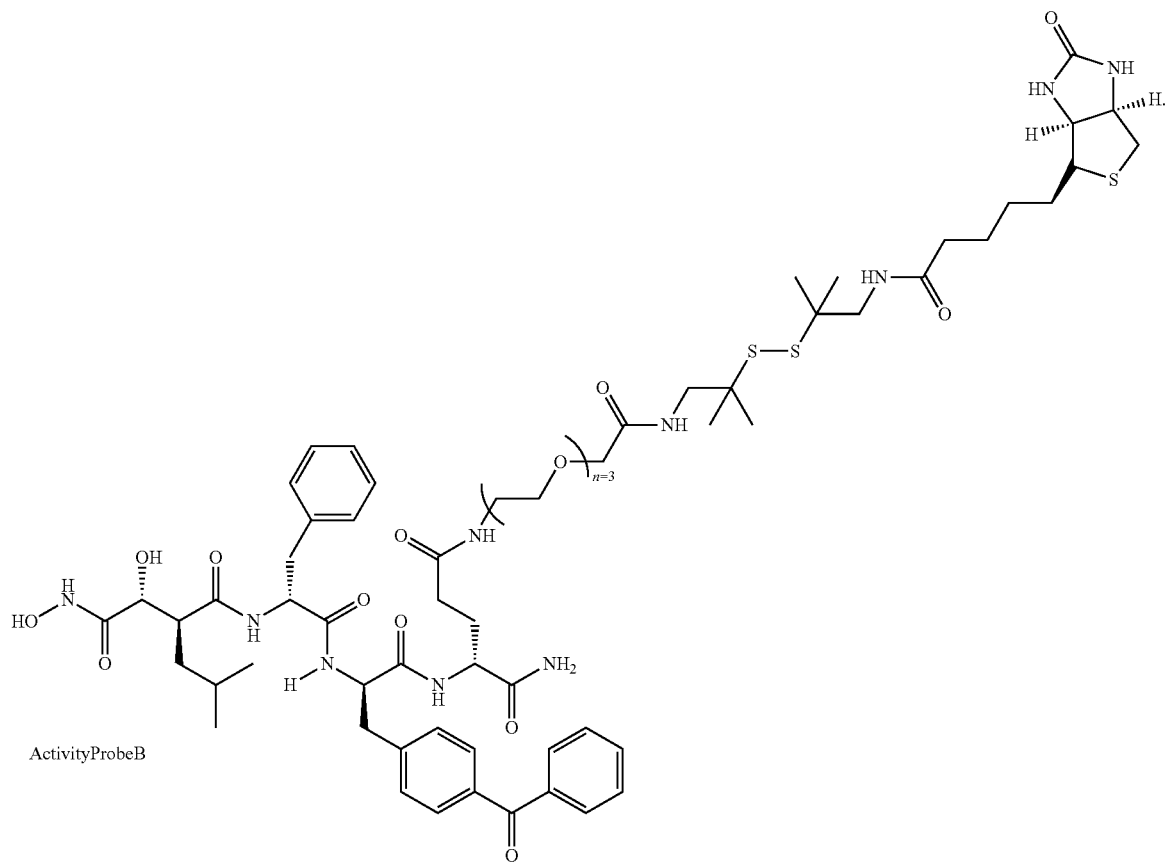

Formula 12

Chemical structure of ActivityProbeB

Figure 15:
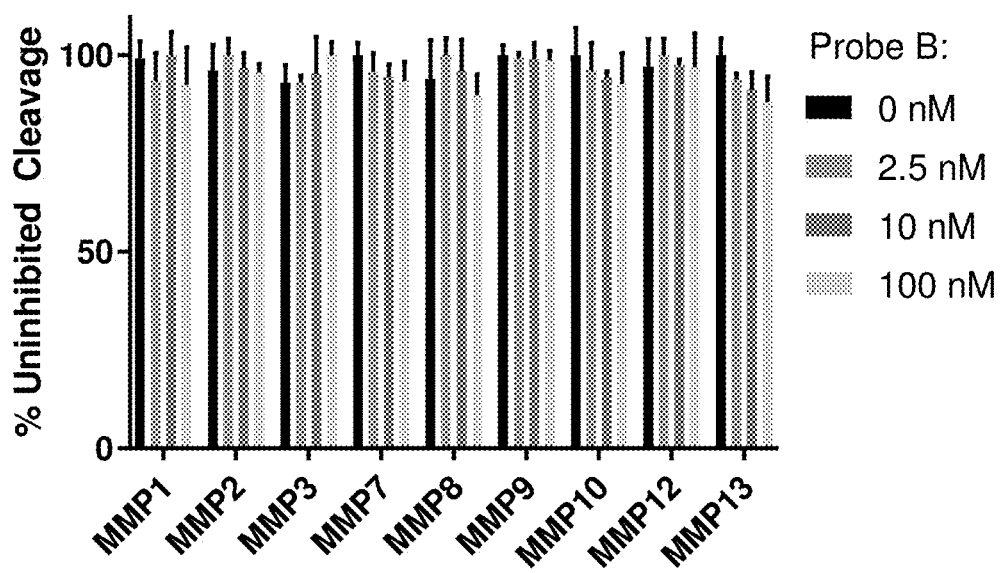
FIG. 15 is a bar graph showing the percent of cleavage of substrate by different MMPs in the absence (0 nM) or presence (2.5 nM, 10 nM, or 100 nM) of ActivityProbeB, whose structure is shown in Example 6.

FIG. 15 shows up to 100 nM ActivityProbeB did minimal inhibition of a panel of MMPs in cleaving FRET substrates, ActivityProbeB was a lower affinity probe compared to HxBP-Bt. It can be used for screening the selectivity of competitive protease inhibitors as small molecule therapeutics.

Another alternative activity-based probed is denoted as ActivityProbeC, whose structure is shown below:

multiple MMPs due to the addition of 1 mM or 10 mM EDTA. EDTA supplemented wash buffer elutes the activity probe from the immobilized active MMP by chelating the Zinc cation from the MMP active site. Without the Zinc cation present to bind the hydroxamate group of the activity-based probe, the activity-based probe readily washes away.

FIG. 17 shows a schematic workflow of enrichment and release of active MMPs. An activity-based probe containing

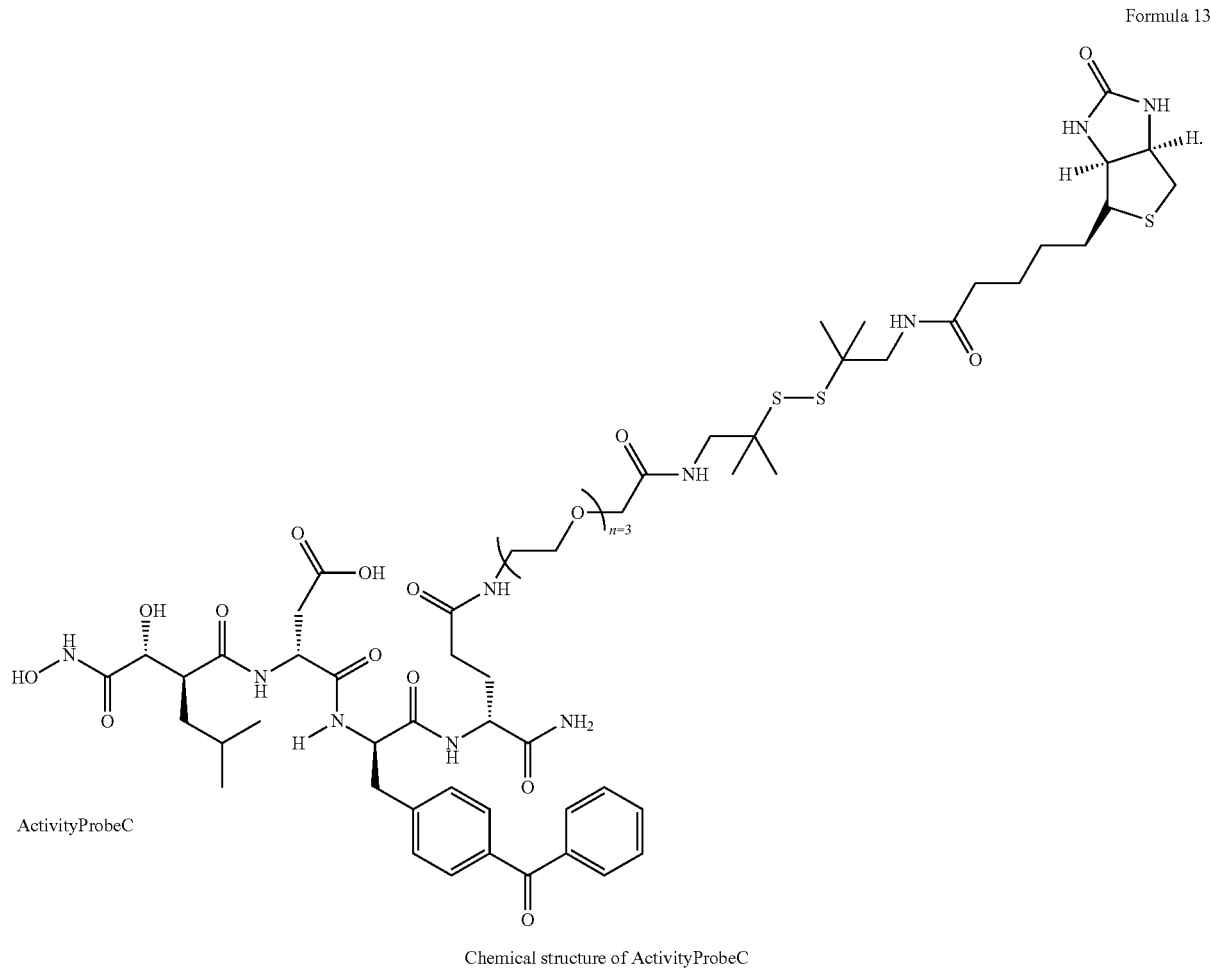

Chemical structure of ActivityProbeC

Figure 16:
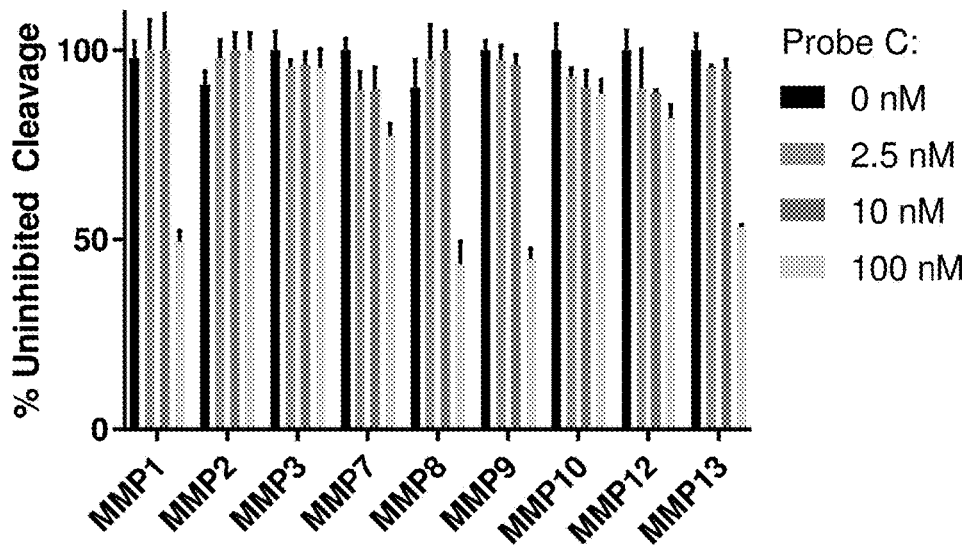
FIG. 16 is a bar graph showing the percent of cleavage of substrate by different MMPs in the absence (0 nM) or presence (2.5 nM, 10 nM, or 100 nM) of ActivityProbeC, whose structure is shown in Example 6.

FIG. 16 shows ActivityProbeC (100 nM) notably inhibited FRET substrate cleavage of MMPs 1, 7, 8, 9, and 13.

Inhibition of MMP activity of ActivityProbeB and ActivityProbeC was significantly lower than that observed for the Biotin-Tagged Hydroxamate Benzophenone (HxBP-Bt) Probe with a PEG linker. These probes were able to integrate with the MAMBI assay to detect MMPs with lower overall fluorescent signal.

Figure 18A:
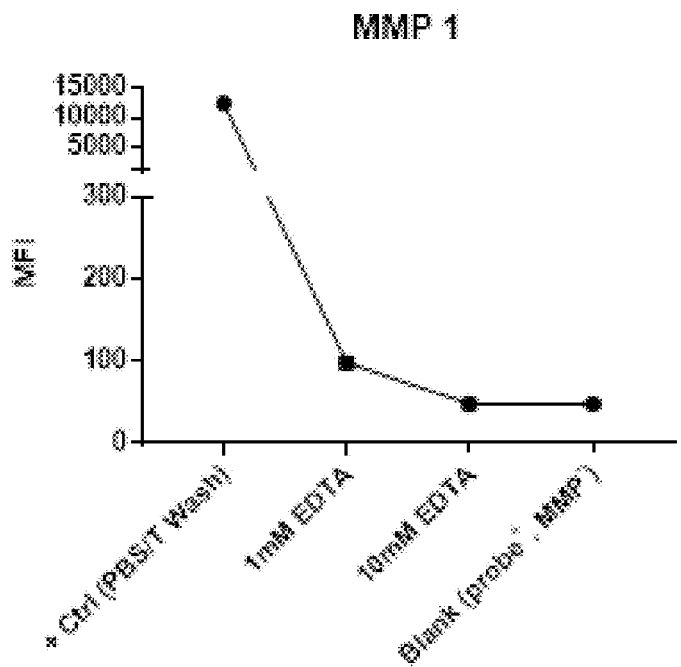
FIG. 18A is a line graph showing the amount of fluorescent signal that remains in the assay as shown in FIG. 1A after different wash solutions: a phosphate-buffered saline containing TWEEN® (PBS/T wash; control wash); an elution buffer of PBS/T supplemented with 1 mM EDTA; an elution buffer of PBS/T supplemented with 10 mM EDTA; and blank (containing activity-based probe without MMP present). EDTA supplemented wash buffer elutes the activity-based probe from the immobilized active MMP by chelating the zinc cation from the MMP active site. Without the zinc cation present to bind the hydroxamate group of the activity-based probe, the activity-based probe readily washes away.
Figure 18B:
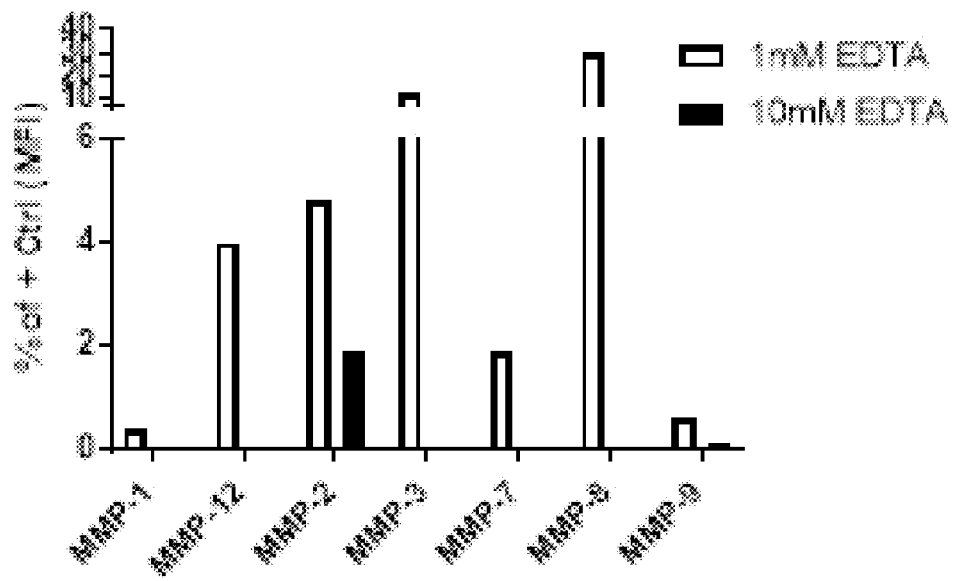
FIG. 18B is a bar graph showing the residual fluorescence for multiple MMPs after 1 mM or 10 mM EDTA wash as a percentage compared to a control wash in PBS/T.
Figure 19A:
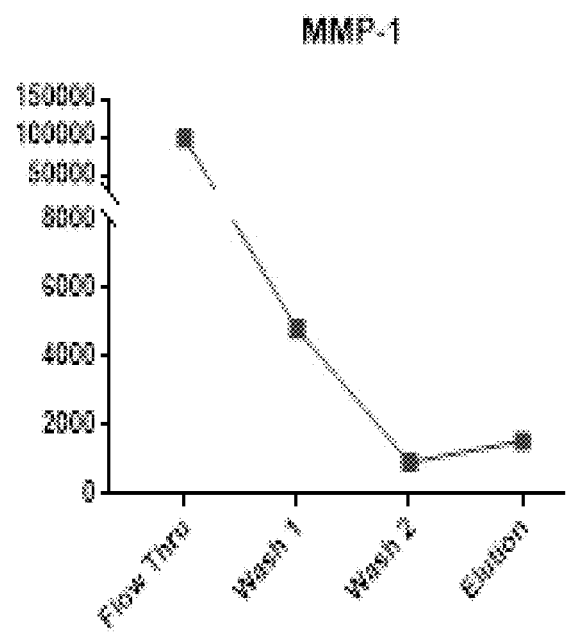
FIGS. 19A-19H are dot plots showing the fluorescence signal obtained from the assay as shown in FIG. 17. A cocktail containing active and inactive MMPs was incubated with activity-based probes tethered to magnetic beads. The fluorescent signals in the unbound fraction (flow-through, "Flow Thru") representing inactive MMPs, in the first wash, in the second wash, and in the elution were assayed as shown in FIG. 17 for active MMP-1 (FIG. 19A), active MMP-2 (FIG. 19B), active MMP-3 (FIG. 19C), active MMP-7 (FIG. 19D), active MMP-8 (FIG. 19E), active MMP-9 (FIG. 19F), active MMP-10 (FIG. 19G), and active MMP-12 (FIG. 19H).
Figure 19B:
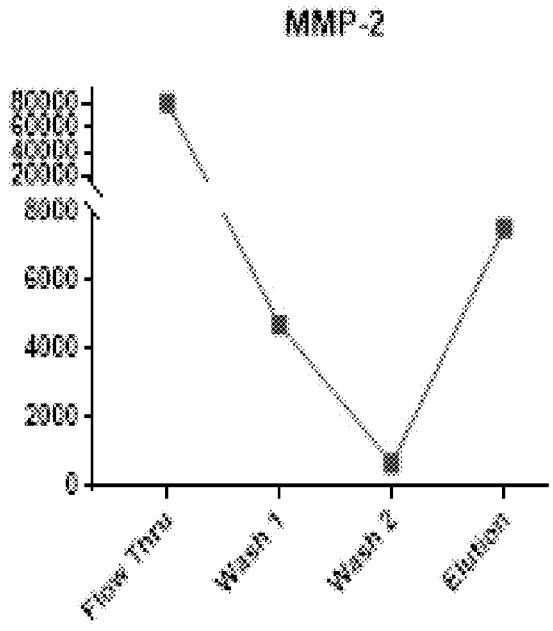
Figure 19C:
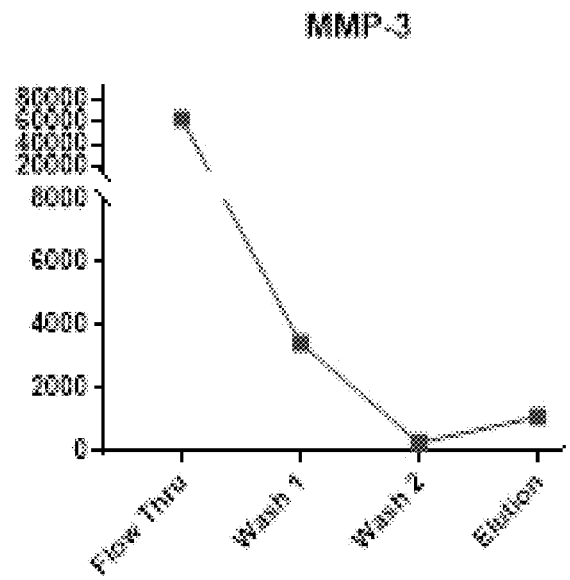
Figure 19D:
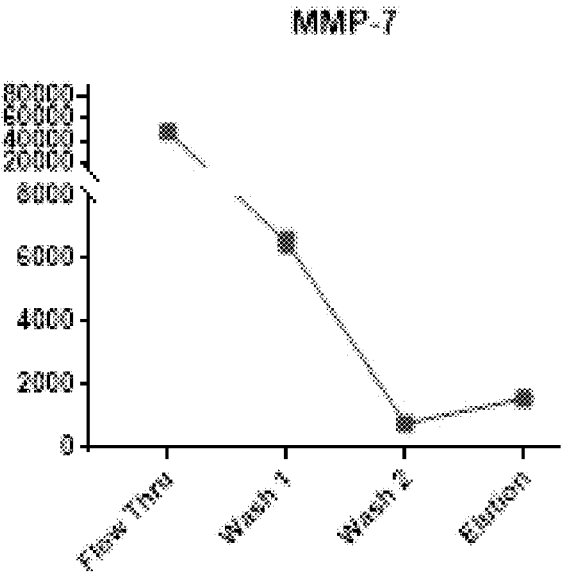
Figure 19E:
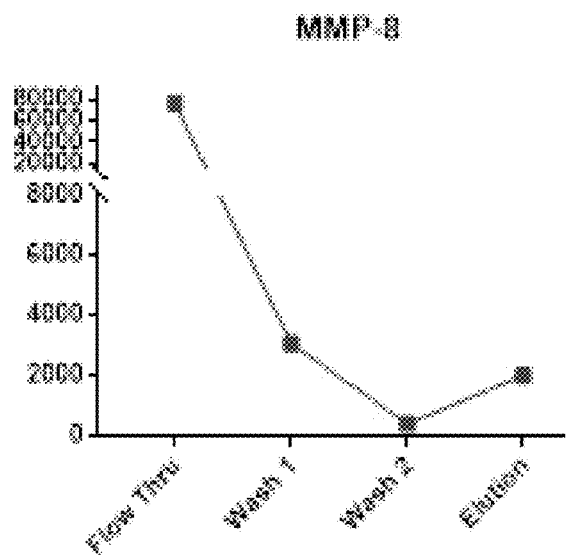
Figure 19F:
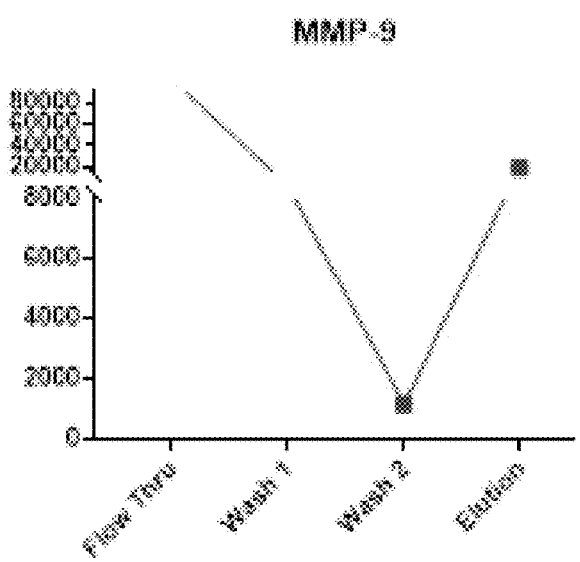
Figure 19G:
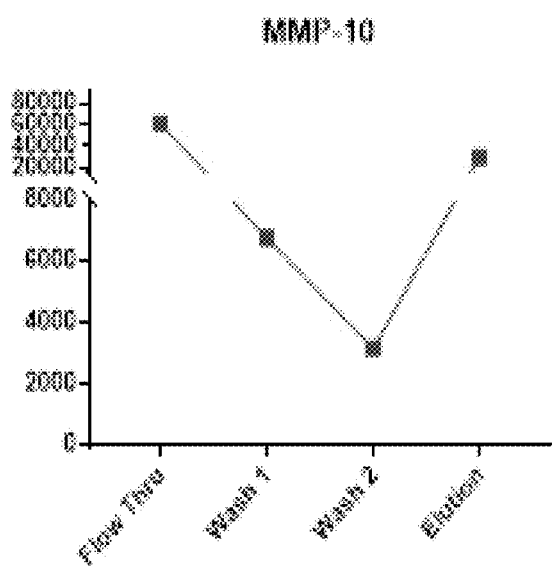
Figure 19H:
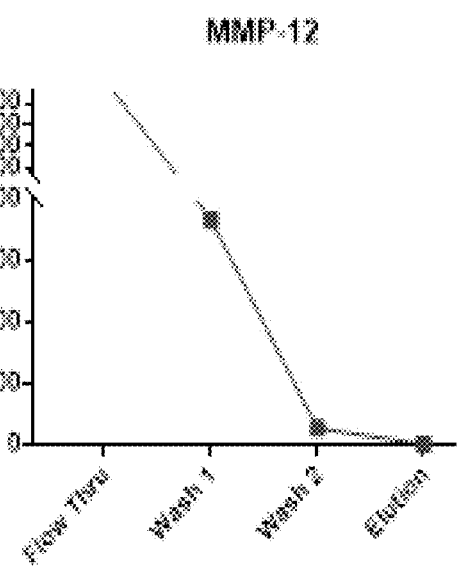

Example 7. Validation of Enriching Active MMPs Prior to Identification and Quantification in a Multiplex Assay FIG. 18A shows the reduction of MAMBI fluorescence when EDTA was added to the wash steps, validating that EDTA disrupts the association between the active protease and the activity-based probe in a multiplex reagent assay. FIG. 18B shows the reduction in fluorescence detecting a biotin as a "tag" is associated with the magnet beads, and the beads are coated with one or more biotin-binding proteins (e.g. streptavidin, avidin). The magnetic bead with the bound activity-based probe is then incubated with a mixture of inactive and active MMPs. Inactive MMPs are removed by placing beads under magnetic field and washing. Active MMPs are then eluted from the beads with 10 mM EDTA in wash buffer. The elution fraction is then incubated with encoded particles coated with specific capture reagents (e.g. antibodies), then subsequently detected with biotin labeled antibodies and fluorescent streptavidin.

FIGS. 19A-H demonstrate the enrichment and release of each MMP in an enzyme sample. The flow-through ("Flow Thru") represented inactive MMPs, and each wash fraction shows decreasing presence of MMPs. After elution with EDTA supplemented wash buffer, there was a spike in the fluorescence signal, indicating the release of active enzymes from the activity-based probe tethered to a magnetic bead, for MMP-1, MMP-2, MMP-3, MMP-7, MMP-8, MMP-9, and MMP-10. MMP-12 did not appear compatible with the enrichment and release format. Because the activity-based probe labels MMP-12 sufficiently, as shown in FIG. 5 and FIG. 6, it was likely that EDTA induced a conformational change in active MMP-12 that abrogated binding to the tested version of the MMP-12 capture reagent.

We claim:

1. A reagent set for assaying a plurality of active enzymes in a sample, comprising
   (a) a plurality of activity-based probes, wherein each activity-based probe comprises (1) an active site directed affinity ligand comprising a metalloprotease inhibitor moiety, the moiety comprising a hydroxamate group and optionally a photoactivatable benzophenone, (2) a reporter group comprising biotin, (3) a linker between the active site directed affinity ligand and the reporter group, and optionally, (4) a secondary detectable label, and
      each activity-based probe selectively binds to the active site of a metalloprotease (MMP) or cathepsin, binding only to an active form of the MMP or cathepsin, not to the zymogen form of the MMP or cathepsin nor to the inhibited form of the MMP or cathepsin; and
   (b) a plurality of encoded particle sets, each particle in each set having attached thereto distinct enzyme-identifying molecules, wherein each distinct enzyme-identifying molecule binds a specific type of MMP or cathepsin.

2. The reagent set of claim 1, wherein the active site directed affinity ligand is selected from the group consisting of an antibody against the active site of the metalloprotease or cathepsin, a substrate of the metalloprotease or cathepsin, and an inhibitor of the metalloprotease or cathepsin.

3. The reagent set of claim 1, wherein the encoded particles of one encoded particle set is distinguishably detectable based on one or more properties selected from the group consisting of optical, chemical, physical, electronic, and magnetic properties.

4. The reagent set of claim 1, wherein the active site directed affinity ligand further comprises a group for metal chelation.

5. The reagent set of claim 1, wherein the active site directed affinity ligand further comprises one or more peptides for selectively targeting the conserved nucleophiles in the active site of a cathepsin.

6. The reagent set of claim 1 wherein the metalloprotease (MMP) is selected from the group consisting of MMP1, MMP2, MMP3, MMP7, MMP9, MMP10, MMP12, and MMP13.

7. The reagent set of claim 1, wherein the distinct enzyme-identifying molecule is selected from the group consisting of antibodies and aptamers.

8. The reagent set of claim 1, wherein the distinct enzyme identifying molecules of one encoded particle set is distinguishably detectable from another distinct enzyme identifying molecules of another encoded particle set based on one or more properties selected from the group consisting of optical, chemical, physical, electronic, and magnetic properties.

9. The reagent set of claim 1, wherein the distinct enzyme identifying molecules are detectable in a tissue sample.

10. The reagent set of claim 1 wherein the metalloprotease or cathepsin is associated with endometriosis or preeclampsia.

11. The reagent set of claim 1, wherein the tissue is endometrium.

12. The reagent set of claim 1, wherein following incubation of the sample containing the activity-based probes described in (a) and the plurality of encoded particles with attached distinct enzyme-identifying molecules described in (b), the distinct enzyme-identifying molecules can identify and quantify specific types of active MMP or cathepsin in the sample.

13. The reagent set of claim 1, wherein the linker between the active site directed affinity ligand and the reporter group is polyethylene glycol (PEG).

* * * * *